US011357851B2

(12) United States Patent
Hatakeyama et al.

(10) Patent No.: US 11,357,851 B2
(45) Date of Patent: Jun. 14, 2022

(54) USES OF MYOSTATIN ANTAGONISTS, COMBINATIONS CONTAINING THEM AND USES THEREOF

(71) Applicant: Novartis AG, Basel (CH)

(72) Inventors: Shinji Hatakeyama, Basel (CH); Ronenn Roubenoff, Brookline, MA (US); Estelle Trifilieff, Dietwiller (FR); Jerome Feige, Village Neuf (FR); Lloyd B. Klickstein, Newton, MA (US)

(73) Assignee: Novartis AG, Basel (CH)

( * ) Notice: Subject to any disclaimer, the term of this patent is extended or adjusted under 35 U.S.C. 154(b) by 61 days.

(21) Appl. No.: 15/774,327

(22) PCT Filed: Nov. 9, 2016

(86) PCT No.: PCT/IB2016/056744
§ 371 (c)(1),
(2) Date: May 8, 2018

(87) PCT Pub. No.: WO2017/081624
PCT Pub. Date: May 18, 2017

(65) Prior Publication Data
US 2020/0254090 A1 Aug. 13, 2020

Related U.S. Application Data

(60) Provisional application No. 62/253,896, filed on Nov. 11, 2015.

(51) Int. Cl.
*A61K 39/395* (2006.01)
*A61P 21/00* (2006.01)
*A61P 35/00* (2006.01)
*A61K 33/243* (2019.01)
*A61K 31/436* (2006.01)

(52) U.S. Cl.
CPC ........ *A61K 39/3955* (2013.01); *A61K 31/436* (2013.01); *A61K 33/243* (2019.01); *A61P 21/00* (2018.01); *A61P 35/00* (2018.01)

(58) Field of Classification Search
None
See application file for complete search history.

(56) References Cited

U.S. PATENT DOCUMENTS

| | | | |
|---|---|---|---|
| 3,929,992 A | 12/1975 | Sehgal et al. | |
| 5,665,772 A | 9/1997 | Cottens et al. | |
| 6,015,815 A | 1/2000 | Mollison | |
| 7,091,213 B2 | 8/2006 | Metcalf, III et al. | |
| 7,252,821 B2 * | 8/2007 | Young | C07K 16/2884 424/141.1 |
| 8,388,968 B2 | 3/2013 | Berger et al. | |
| 8,551,482 B2 | 10/2013 | Berger et al. | |
| 2005/0101624 A1 | 5/2005 | Betts et al. | |
| 2006/0216279 A1 | 9/2006 | Glass et al. | |
| 2009/0149511 A1 * | 6/2009 | Burk | A61K 38/13 514/357 |
| 2013/0344091 A1 | 12/2013 | Berger et al. | |
| 2016/0031993 A1 | 2/2016 | Berger et al. | |
| 2018/0194846 A1 | 7/2018 | Berger et al. | |

FOREIGN PATENT DOCUMENTS

| | | | | |
|---|---|---|---|---|
| EP | 2589385 | * | 5/2013 | ........ A61K 31/4439 |
| WO | WO-94/09010 A1 | | 4/1994 | |
| WO | WO-95/14023 A1 | | 5/1995 | |
| WO | WO-95/16691 A1 | | 6/1995 | |
| WO | WO-96/41807 A1 | | 12/1996 | |
| WO | WO-98/02441 A2 | | 1/1998 | |
| WO | WO-98/02441 A3 | | 1/1998 | |
| WO | WO-99/15530 A1 | | 4/1999 | |
| WO | WO-01/14387 A1 | | 3/2001 | |
| WO | 2007/067616 A2 | | 6/2007 | |
| WO | 2013/063536 A1 | | 5/2013 | |
| WO | WO2013/063536 | * | 5/2013 | ............. C07K 16/28 |
| WO | 2013/106175 A1 | | 7/2013 | |
| WO | 2014/121221 A1 | | 8/2014 | |
| WO | 2015/111008 A2 | | 7/2015 | |
| WO | 2015/162590 A1 | | 10/2015 | |
| WO | WO-2015/162590 A1 | | 10/2015 | |

OTHER PUBLICATIONS

Cesari et al., Pharmacological interventions in frailty and sarcopenia: report by the International Conference on frailty and sarcopenia research task force. J. Frailty Aging, 4, 114-120, 2015-ePub Sep. 9, 2015. (Year: 2015).*
Rachner et al., Cancer-targeted therapies and radiopharmaceuticals. BoneKEy Reports 4, Art. No. 707, 2015. (Year: 2015).*
Zhou et al.,Reversal of cancer cachexia and muscle wasting by ActRIIB antagonism leads to prolonged survival. Cell, 142, 531-543, 2010. (Year: 2010).*
Trifilieff et al.,An antibody blocking Activin type II receptors induces strong skeletal muscle hypertrophy and protects from atrophy. Mol. Cell. Biol. 34, 606-618, 2014. (Year: 2014).*
Costello B. A. et al., "Phase 1 trial of everolimus, gemcitabine and cisplatin in patients with solid tumors," Invest. New Drugs, 32:710-716, 2014.
Zhou et al.,Reversal of cancer cachexia and muscle wasting by ActRIIB antagonism leads to prolonged survival. Cell, 142, 531-543, 2010. (Year: 2010).*
Trifilieff et al.,An antibody blocking Activin type II receptors induces strong skeletal muscle hypertrophy and protects from atrophy. Mol. Cell. Biol. 34, 606-618, 2014. (Year: 2014).*
Costello B. A. et al., "Phase 1 trial of everolimus, gemcitabine and cisplatin in patients with solid tumors," Invest. New Drugs, 32:710-716, 2014.

(Continued)

*Primary Examiner* — Elly-Gerald Stoica
(74) *Attorney, Agent, or Firm* — Cooley LLP

(57) ABSTRACT

The present invention relates to myostatin antagonists, for the treatment of cancer cachexia, and cancer cachexia due to chemotherapeutic treatment. In particular, the myostatin antagonist bimagrumab was found to be beneficial in the treatment of cancer cachexia by reducing body weight loss. The present invention also relates to combinations and uses of a myostatin antagonist and an mTOR inhibitor for treating cancer cachexia by reducing, maintaining or increasing body weight loss or for use in treating age-related conditions.

11 Claims, 5 Drawing Sheets

Specification includes a Sequence Listing.

(56) References Cited

OTHER PUBLICATIONS

Zhou et al., "Reversal of cancer cachexia and muscle wasting by ActRIIB antagonism leads to prolonged survival", Cell, 2010, vol. 142, pp. 531-543.
Cesari et al., "Pharmacological interventions in frailty and sarcopenia: report by the international conference on frailty and sarcopenia research task force", on behalf of the International Conference on Frailty and Sarcopenia Research Task Force HHS Public Access, 2015, pp. 114-120.
Mannick et al., "mTOR inhibition improves immune function in the elderly", Immunology, 2014, vol. 6, No. 268, 268ra179.
Morgan et al., "RAD001 (Everolimus) inhibits growth of prostate cancer in the bone and in the inhibitory effects are increased by combination with docetaxel and zoledronic acid", Prostate, 2008, vol. 68, No. 8, pp. 861-871.
Dingemans et al., "Phase II drugs that are currently in development for the treatment of cachexia", Expert Opinion on Investigational Drugs, 2014, vol. 23, No. 12, pp. 1655-1669.
Hatakeyama et al., "ActRII blockade protects mice from cancer cachexia and prolongs survival in the presence of anti-cancer treatments", Skeletal Muscle, 2016, vol. 6, No. 26, pp. 1-12.
Amato, A. A. et al. (2014). Treatment of sporadic inclusion body myositis with bimagrumab. Neurology 83:2239-2246.
Argadine, H. M. (2011). "Intracellular signaling pathways regulating net protein balance following diaphragm muscle denervation," Am. J. Physiol. Cell Physiol. 300:C318-327.
Arrieta O. et al. (2015). "Nutritional Status, Body Surface, and Low Lean Body Mass/Body Mass Index Are Related to Dose Reduction and Severe Gastrointestinal Toxicity Induced by Afatinib in Patients with Non-Small Cell Lung Cancer," The Oncologist 20:967-974.
Benny Klimek, M. E. et al. (2010). Acute inhibition of myostatin-family proteins preserves skeletal muscle in mouse models of cancer cachexia. Biochem. Biophys. Res. Commun. 391:1548-1554.
Bentzinger, C. F. et al. (2008). "Skeletal muscle-specific ablation of raptor, but not of rictor, causes metabolic changes and results in muscle dystrophy," Cell Metab. 8:411-424.
Busquets, S. et al. (2012). "Myostatin blockage using actRIIB antagonism in mice bearing the Lewis lung carcinoma results in the improvement of muscle wasting and physical performance," J. Cachexia Sarcopenia Muscle 3:37-43.
Chen, J. L. et al. (2014). "Elevated expression of activins promotes muscle wasting and cachexia," FASEBJ. 28:1711-1723.
Chou, T. C. et al. (1984). "Quantitative analysis of dose-effect relationships: The combined effects of multiple drugs or enzyme inhibitors," Adv. Enzyme Regul. 22: 27-55.
Drake, J. C. (2010). "AICAR treatment for 14 days normalizes obesity-induced dysregulation of TORC1 signaling and translational capacity in fasted skeletal muscle," Am. J. Physiol. Regul. Integr. Comp. Physiol. 299:1546-1554.
Elkina, Y. (2011). "The role of myostatin in muscle wasting: an overview. J. Cachexia Sarcopenia Muscle," 2:143-151.
Fearon, K. et al. (2011). "Definition and classification of cancer cachexia: an international consensus," Lancet Uncool. 12:489-495.
Holford, N.H.G. et al. (1981). "Understanding the dose-effect relationship: Clinical application of pharmacokinetic-pharmacodynamic models," Clin. Pharmacokinet. 6:429-453.
International Search Report dated May 3, 2017, for PCT Application No. PCT/IB2016/056744, filed on Nov. 9, 2016, 9 pages.
Khamzina, L. (2005). "Increased activation of the mammalian target of rapamycin pathway in liver and skeletal muscle of obese rats: possible involvement in obesity-linked insulin resistance," Endocrinology 146:1473-1481.
Lach-Trifilieff, E. et al. (2014). "An antibody blocking activin type II receptors induces strong skeletal muscle hypertrophy and protects from atrophy," Mol. Cell. Bio. 34:606-618.
Lee, S.J. (2011). "Regulation of myostatin activity and muscle growth," PNAS 98:9306-9311.
Lee, S. J. et al. (2005). "Regulation of muscle growth by multiple ligands signaling through activin type II receptors," PNAS 102:18117-18122.
Loewe, S. et al. (1926). "Loewe additivity," Arch. Exp. Pathol Pharmacol. 114:313-326 (with English Abstract).
MacDonald, E. M. et al. (2014). "Denervation atrophy is independent from Akt and mTOR activation and is not rescued by myostatin inhibition," Dis. Model. Mech. 7:471-481.
Machida, M. et al. (2012). "Reduction of ribosome biogenesis with activation of the mTOR pathway in denervated atrophic muscle," J. Cell Physiol. 227:1569-1576.
Markofski M. et al. (2015). "Effect of age on basal muscle protein synthesis and mTORC1 signaling in a large cohort of young and older men and women," Exp. Geront. 65:1-7.
McAlpine, J.B. et al. (1991). "Revised NMR assignments for Rapamycin," J. Antibiotics 44: 688-690.
Murphy, K. T. et al. (2011). "Antibody-directed myostatin inhibition enhances muscle mass and function in tumor-bearing mice," Am. J. Physiol. Regul. Integr. Comp. 301:R716-R726.
Nacarelli, T. (2015). "Aberrant mTOR activation in senescence and aging: A mitochondrial stress response?" Exp. Gerontol. 68:66-70.
Nakatani, M. et al. (2007). "Transgenic expression of a myostatin inhibitor derived from follistatin increases skeletal muscle mass and ameliorates dystrophic pathology in mdx mice," FASEB J. 22:477-487.
Parsons H.A. (2012). "Evaluation of the clinical relevance of body composition parameters in patients with cancer metastatic to the liver treated with hepatic arterial infusion chemotherapy," Nutr Cancer 64:206-217.
Reis, F. M. et al. (2002). "Serum and tissue expression of activin a in postmenopausal women with breast cancer," J. Clin. Endocrinol. Metab. 87:2277-2282.
Risson, V. et al. (2009). "Muscle inactivation of mTOR causes metabolic and dystrophin defects leading to severe myopathy," J. Cell Biol. 187:859-874.
Schuelke, M. et al. (2004). "Myostatin mutation associated with gross muscle hypertrophy in a child," N. Engl. J. Med. 350:2682-2688.
Sjoblom, B. et al. (2015). "Low muscle mass is associated with chemotherapy-induced haematological toxicity in advanced non-small cell lung cancer," Lung Cancer 90:85-91.
Tan, B. (2009). "Sarcopenia in an overweight or obese patient is an adverse prognostic factor in pancreatic cancer," Clin. Cancer Res. 15:6973-6979.
Tang, H. et al. (2014). "mTORC1 promotes denervation-induced muscle atrophy through a mechanism involving the activation of FoxO and E3 ubiquitin ligases," Sci. Signal. 7:ra18.
Tsai, S. (2012). "Importance of lean body mass in the oncologic patient," Nutr. Clin. Pract. 27:593-598.
Uezumi, A. et al. (2010). "Mechanism and therapeutic application against skeletal muscle atrophy in aging and diseases," Biomedical Gerontology 34:5-11 (with English Abstract).
Van Duyne, G.D. et al. (1991). "Atomic structure of the Rapamycin human immunophilin FKBP-12 complex," J. Am. Chem. Soc. 113: 7433-7434.
Whittemore, L.A. et al. (2003). "Inhibition of myostatin in adult mice increases skeletal muscle mass and strength," Biochem. Biophys. Res. Commun. 300:965-971.
Written Opinion of the International Searching Authority dated May 3, 2017, for PCT Application No. PCT/IB2016/056744, filed on Nov. 9, 2016, 12 pages.
Zimmers, T. A. et al. (2002). "Induction of cachexia in mice by systemically administered myostatin," Science 296:1486-1488.
Office Action for JP Application No. 2018-524218, dated Nov. 10, 2020, 4 pages.
Office Action for JP Application No. 2018-524218, dated Nov. 10, 2020, 3 pages (English Translation).
Egerman, M.A. et al. (2014). "Signaling pathways controlling skeletal muscle mass," Crit. Rev. Biochem. Mol. Biol. 49:59-68. (Published online Nov. 18, 2013).

(56) References Cited

OTHER PUBLICATIONS

Joseph, G.A. et al. (2019). "Partial Inhibition of mTORC1 in Aged Rats Counteracts the Decline in Muscle Mass and Reverses Molecular Signaling Associated with Sarcopenia," Molecular and Cellular Biology 39:1-16.

* cited by examiner

USES OF MYOSTATIN ANTAGONISTS, COMBINATIONS CONTAINING THEM AND USES THEREOF

FIELD OF THE INVENTION

The present disclosure relates to the use of myostatin or activin antagonists and in particular of activin type II (ActRII) receptor inhibitors in the treatment of cancer cachexia. The invention relates more specifically to combinations comprising (a) an activin type II receptor (ActRII) inhibitor and (b) a chemotherapeutic agent or a pharmaceutically acceptable salt thereof, for simultaneous, separate or sequential use, uses thereof, or methods of treatment using it, in the treatment of cancer cachexia.

The disclosure also relates to combinations uses thereof of a myostatin antagonist and an mTOR inhibitor. Such a combined uses are for use in cancer cachexia and for age-related conditions.

BACKGROUND OF THE INVENTION

Cachexia affects the majority of patients with advanced cancer and is associated with a poor outcome, a reduction in treatment tolerance, response to therapy, quality of life and duration of survival. Skeletal muscle loss appears to be the most significant event in cancer cachexia and cannot be fully reversed by conventional nutritional support [Fearon et al 2011, Tan et al 2009]. Recently, it has been shown in mouse models of ectopic lung and colon cancer, that direct myostatin inhibition with a monoclonal antibody as well as indirect inhibition using a soluble ActRIIB-Fc protects from muscle wasting and even extends survival [Benny Klimek et al 2010, Busquets et al 2012, Murphy et al 2011, Zhou et al 2010].

Several members of the transforming growth factor beta (TGF-13) superfamily, including myostatin, Activin A, and growth differentiation factor 11 (GDF-11), are known to negatively regulate skeletal muscle mass in animals and humans throughout the lifecycle. The mechanism of myostatin signaling is complex due to activation of several downstream pathways [Elkina et al 2011]. Myostatin, Activin and GDF-11 bind to activin type II receptors (ActRII) and induce its assembly with activin type I receptor. The absence of myostatin in developing animals and humans results in a hyper-muscular phenotype with an increased number and size of muscle fibers [Lee and McPherron 2001, Schuelke et al 2004]. Similarly, inhibition of myostatin action in adult animals increases muscle mass, suggesting that myostatin also restrains skeletal muscle mass in adulthood [Whittemore et al 2003, Lee et al 2005, Nakatani et al 2008]. In contrast, high levels of myostatin or Activin A have been reported to promote cachexia and the subsequent muscle wasting [Zimmers et al, 2002; Chen et al, 2014].

WO07/067616 shows the reduction of weight loss by the administration of a myostatin-binding agent such as a peptide binding myostatin in normal mice treated with 5-fluorouracil. However it does not show that the peptide binding myostatin reduces body weight loss or increases the body weight in tumor-bearing model mice such as CT-26, either in the absence of or with a treatment using anticancer agents as demonstrated according to the present disclosure.

Bimagrumab is a human monoclonal antibody developed to bind competitively to ActRII with greater affinity than its natural ligands myostatin and activin A. It induces skeletal muscle hypertrophy and protects from dexamethasone-induced atrophy in mice [Lach-Trifilieff et al 2014] and is shown to improve the disease condition in the patients suffering from sporadic inclusion body myositis without causing serious adverse events [Amato et al 2014]. Although it has been shown that the pharmacological blockade of ActRII pathway using a soluble receptor antagonist protects from cancer-induced cachexia in mice [Busquets et al 2012, Zhou et al 2010], cachectic patients with advanced cancer will likely receive anti-cancer agents against their specific cancer type as a standard of care, and whether ActRII inhibition remains efficacious when combined with anticancer agents has not been elucidated yet.

According to the present invention, the effect of a chimeric mouse version of bimagrumab, which is shown to retain the binding, selectivity and potency profile of bimagrumab while reducing risk for immunogenicity and enabling long-term profiling studies in mice, was evaluated in a CT-26 mouse colon cancer cachexia model to clarify interactions between bimagrumab and chemotherapies. Additionally, intervention at the Activin type II receptors level via the use of the neutralizing Ab bimagrumab is effective at protecting from cancer-induced cachexia as reported earlier through the blockade of circulating ligands (anti myostatin Ab or soluble ActRIIB-Fc).

Platinum-based drugs, such as cisplatin, are cytotoxic, intercalating agents that prevent DNA replication in a very unspecific manner and which are typically used as first-line therapy. Problematically, cisplatin has been shown to precipitate body and muscle weight loss as a side effect. We thus first aimed at evaluating the potential of bimagrumab in countering cisplatin-mediated effects on muscle wasting. In a follow-up study, the impact of a more frequent dose of bimagrumab and everolimus, a new generation, less cytotoxic, molecular-targeted agent, which inhibits the mammalian target of rapamycin (mTOR), on cancer cachexia was then assessed.

In addition, loss of muscle mass and attendant loss of total body water (as part of the cachexia pathophysiology) leads to a smaller volume of distribution for chemotherapeutic agents [Parsons 2012]. This in turn causes a higher concentration (Cmax and AUC) of these cytotoxic agents, leading to more adverse events and poorer chemotherapy tolerance in cachectic patients than in noncachectic cancer patients [Sjoblom 2015, Arrieta 2015]. A manifestation of this invention is that it can lead to better chemotherapy tolerance, more effective anti-cancer treatment, and better outcomes (including progression-free survival and overall survival) than with anti-cancer treatment alone in patients with cancer cachexia.

Currently, there is no standard treatment for cancer cachexia.

Therefore, pharmacotherapeutics that can reduce or prevent body weight loss or even increase body weight in the context of cancer, with or without treatment with chemotherapeutic agents, and in particular with mTOR inhibitors are highly desired.

In addition the combination of a myostatin or activin antagonist and of an mTOR inhibitor according to the present disclosure has also the potential to treat age-related conditions.

SUMMARY OF THE INVENTION

A first subject matter of the present disclosure therefore relates to a combination of an ActRII receptor inhibitor and a chemotherapeutic agent for treating cancer cachexia.

Another subject matter of the disclosure therefore relates methods or uses for treating cancer cachexia of compositions comprising a myostatin or activin antagonist, which can be a myostatin binding molecule or an ActRII binding molecule.

According to the present disclosure, the effect of a chimeric mouse version of bimagrumab, which is shown to retain the binding, selectivity and potency profile of bimagrumab while reducing risk for immunogenicity and enabling long-term profiling studies in mice, was evaluated in a CT-26 mouse colon cancer cachexia model to clarify interactions between bimagrumab and chemotherapies. Additionally, intervention at the Activin type II receptors level via the use of the neutralizing Ab bimagrumab is effective at protecting from cancer-induced cachexia as reported earlier through the blockade of circulating ligands (anti myostatin Ab or soluble ActRIIB-Fc).

Platinum-based drugs, such as cisplatin, are cytotoxic, intercalating agents that prevent DNA replication in a very unspecific manner and which are typically used as first-line therapy.

Problematically, cisplatin has been shown to precipitate body and muscle weight loss as a side effect. It was first aimed at evaluating the potential of bimagrumab in countering cisplatin-mediated effects on muscle wasting. In a follow-up study, the impact of a more frequent dose of bimagrumab and everolimus, a new generation, less cytotoxic, molecular-targeted agent, which inhibits the mammalian target of rapamycin (mTOR), on cancer cachexia was then assessed.

Muscle Regulation and the ActRII Receptors

Several members of the transforming growth factor beta (TGF-β) superfamily, including myostatin, activin A, and growth differentiation factor 11 (GDF11), negatively regulate skeletal muscle mass in animals and humans throughout the lifecycle. Ligand signaling occurs via type II activin receptors (both ActRIIA and B; and the Smad 2/3 pathway), to inhibit muscle protein synthesis and myocyte differentiation and proliferation. The absence of any of these ligands in developing animals and humans results in a hypermuscular phenotype with an increased number and size of muscle fibers. A postpartum reduction of myostatin levels results in the hypertrophy of skeletal muscle due to an increase in the size of existing myofibers (Lee et al 2005; Lee et al 2010; Trendelenburg et al 2012). Thus, the capacity for modulating muscle growth by perturbing this signaling pathway at the receptor level is much more substantial than previously appreciated by direct anti-myostatin approaches.

"Myostatin antagonist" as used herein refers to a molecule capable of antagonizing (e.g., reducing, inhibiting, decreasing, delaying) myostatin function, expression and/or signalling (e.g., by blocking the binding of myostatin to the myostatin receptor, i.e., ActRIIB). Non-limiting examples of antagonists include myostatin binding molecules and ActRII (ActRII A ActRIIB, or ActRIIA/B) receptor binding molecules. In some embodiments of the disclosed methods, regimens, kits, processes, uses and compositions, a myostatin antagonist is employed.

By "myostatin binding molecule" is meant any molecule capable of binding to the human myostatin antigen either alone or associated with other molecules. The binding reaction may be shown by standard methods (qualitative assays) including, for example, a binding assay, competition assay or a bioassay for determining the inhibition of myostatin binding to its receptor or any kind of binding assays, with reference to a negative control test in which an antibody of unrelated specificity, but ideally of the same isotype, e.g., an anti-CD25 antibody, is used. Non-limiting examples of myostatin binding molecules include small molecules, myostatin receptor decoys, and antibodies that bind to myostatin as produced by B-cells or hybridomas and chimeric, CDR-grafted or human antibodies or any fragment thereof, e.g., F(ab')$_2$ and Fab fragments, as well as single chain or single domain antibodies. Preferably the myostatin binding molecule antagonizes (e.g., reduces, inhibits, decreases, delays) myostatin function, expression and/or signalling. In some embodiments of the disclosed methods, regimens, kits, processes, uses and compositions, a myostatin binding molecule is employed. By "ActRII receptor inhibitor" is meant any molecule capable of binding to the human ActRII receptor (ActRII A and/or ActRIIB) either alone or associated with other molecules and inhibiting the receptor signalling. The binding and inhibiting reactions may be shown by standard methods (qualitative assays) including, for example, a binding assay, competition assay or a bioassay for determining the inhibition of ActRII receptor binding to myostatin or any kind of binding assays, with reference to a negative control test in which an antibody of unrelated specificity, but ideally of the same isotype, e.g., an anti-CD25 antibody, is used. Non-limiting examples of ActRII receptor inhibitors include small molecules, myostatin decoys, and antibodies to the ActRII receptor as produced by B-cells or hybridomas and chimeric, CDR-grafted or human antibodies or any fragment thereof, e.g., F(ab')$_2$ and Fab fragments, as well as single chain or single domain antibodies. Preferably the ActRII receptor binding molecule antagonizes (e.g., reduces, inhibits, decreases, delays) myostatin/activing function, expression and/or signalling. In some embodiments of the disclosed combinations, uses, methods and compositions, an ActRII receptor inhibitor is employed.

Bimagrumab

Bimagrumab, the pharmaceutically active compound used in accordance with the present invention, is a fully human, monoclonal antibody (modified IgG1, 234-235-Ala-Ala, λ2) developed to bind competitively to activin receptor type II (ActRII) with greater affinity than its natural ligands that limit muscle mass growth, including myostatin and activin. Bimagrumab is cross-reactive with human and mouse ActRIIA and ActRIIB and effective on human, cynomolgus, mouse and rat skeletal muscle cells. Bimagrumab binds with extremely high affinity (KD 1.7±0.3 pM) to human ActRIIB and with relatively lower affinity to human ActRIIA (KD 434±25 pM).

The present invention is based on the therapeutic approach that sufficiently blocking myostatin binding to its receptor ActRII (ActRIIB and/or ActRIIA) will significantly reduce the activity of myostatin and other ligands that inhibit skeletal muscle growth acting at the receptors, while allowing some of those ligands to perform their other physiologic functions via secondary receptors (Upton et al 2009). Other approaches to reducing myostatin activity, i.e. competitive soluble ActRII, creating a soluble receptor sink may deplete a range of ActRII ligands with activities at other receptors, potentially creating a greater safety risk than using a receptor antagonist antibody like bimagrumab.

Other approaches include the use of or antibodies binding myostatin such as LY2495655 (Eli Lilly), which will then inhibit or reduce signalling through the ActRII receptor.

As a potent inhibitor of ActRII, bimagrumab blocks the effects of myostatin, activin A, GDF11, and possibly other ligands working through this receptor.

The present invention therefore provides inter alia a myostatin antagonist or an activin (such as activin A, activin B or activin AB) antagonist preferably a myostatin binding molecule or antibody, and more preferably an inhibitor or more preferably an anti-ActRII receptor antibody, most preferably bimagrumab, for use in the treatment of cancer cachexia.

BRIEF DESCRIPTION OF THE DRAWINGS

In the following the present invention is described in detail with reference to accompanying figures in which.

Figure 1:
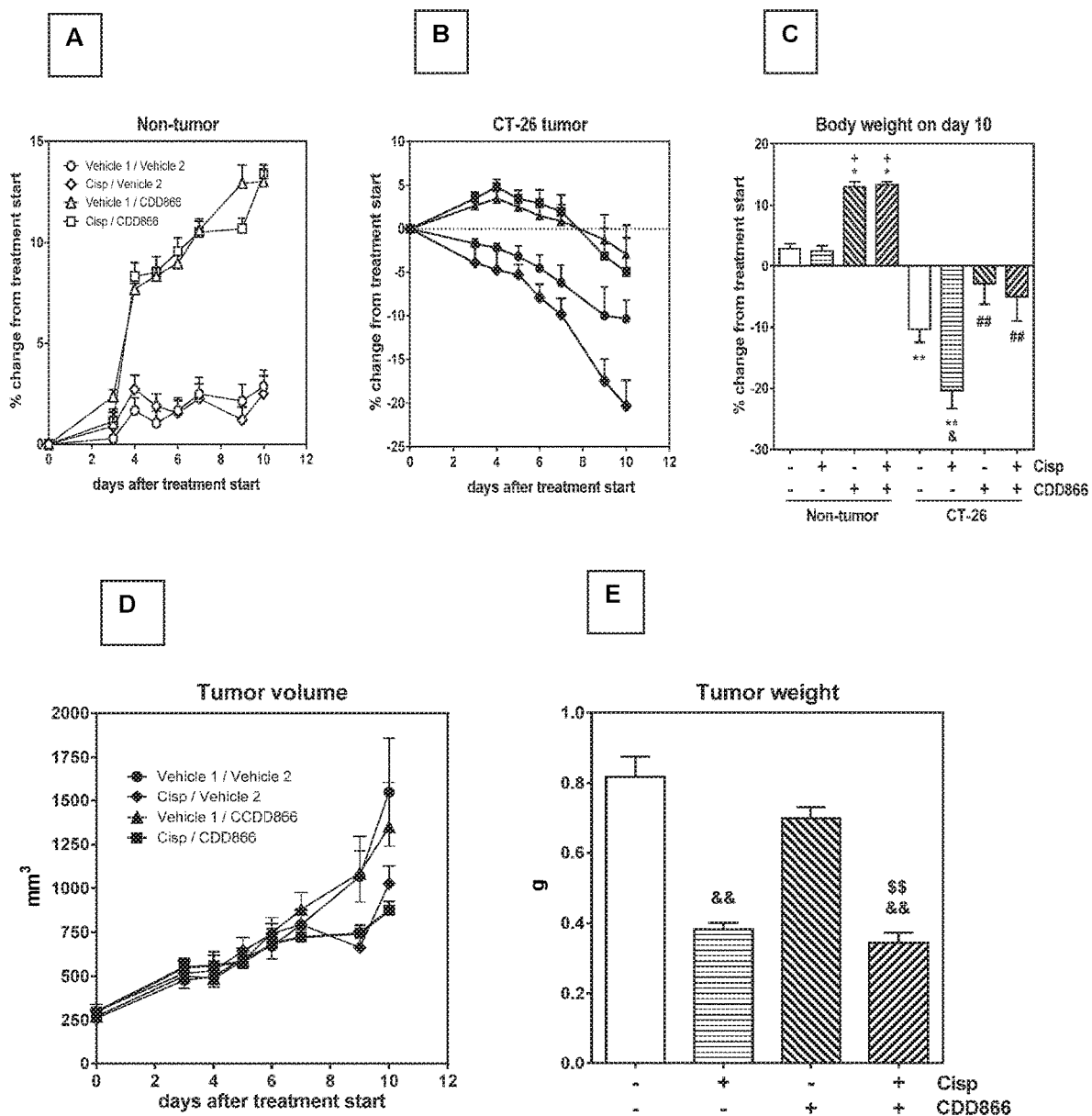
FIG. 1: The effects of cisplatin and CDD866 on body weight (A, B, C), tumor volume (D) and weight (E) in CT-26 mouse colon cancer-induced cachexia, either alone or in combination. Values are expressed as means±SEM (n=10). Percent changes of body weight were calculated in comparison to treatment start on day 0; *: P<0.05, **: P<0.01 versus Non-tumor control; $^{\&\&}$: P<0.01 versus CT-26 control; $^{++}$: P<0.01 versus Non-tumor cisplatin; $^{\#\#}$: P<0.01 versus CT-26 cisplatin by Sidak's multiple comparison test following ANOVA.

1. mTOR is overactive in skeletal muscle of old vs young rats.
2. mTOR is not appropriately down regulated after fasting in the skeletal muscle of old vs young rats.

DETAILED DESCRIPTION OF THE INVENTION

The present invention pertains to a combination comprising (a) an activin receptor type II receptor inhibitor, and (b) a chemotherapeutic agent, or a pharmaceutically acceptable salt thereof, and uses thereof, for simultaneous, separate or sequential use for the treatment of cancer cachexia in a subject.

It also pertains to the combination of (a) a moystatin or activin antagonist and (b) an mTOR inhibitor for treating age-related conditions.

The combination can be fixed or non-fixed, preferably non-fixed.

The general terms used herein are defined with the following meanings, unless explicitly stated otherwise:

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The term "combination" or "pharmaceutical combination" is defined herein to refer to either a fixed combination in one dosage unit form, a non-fixed combination or a kit of parts for the combined administration where an activin type II receptor (ActRII) antagonist or blocker, and a chemotherapeutic agent, or pharmaceutically acceptable salt thereof may be administered independently at the same time or separately or sequentially within time intervals that allow that the combination partners show a cooperative, e.g., additive or synergistic, effect.

The term "fixed combination" means that the active ingredients or therapeutic agents, are administered to a patient simultaneously in the form of a single entity or dosage form.

The term "non-fixed combination" means that the active ingredients or therapeutic agents, are both administered to a patient as separate entities or dosage forms either simultaneously, concurrently or sequentially with no specific time limits, wherein such administration provides therapeutically effective levels of the three compounds in the body of the subject, e.g., a mammal or human, in need thereof.

Preferably herein the term "combination" or "pharmaceutical combination" is a non-fixed combination.

The term "pharmaceutical composition" is defined herein to refer to a mixture or solution containing at least one therapeutic agent to be administered to a subject, e.g., a mammal or human, in order to treat a particular disease or condition affecting the subject thereof.

The term "pharmaceutically acceptable" is defined herein to refer to those compounds, biologic agents, materials, compositions and/or dosage forms, which are, within the scope of sound medical judgment, suitable for contact with the tissues a subject, e.g., a mammal or human, without excessive toxicity, irritation allergic response and other problem complications commensurate with a reasonable benefit/risk ratio.

The terms "combined administration" as used herein are defined to encompass the administration of the selected therapeutic agents to a single subject, e.g., a mammal or human, and are intended to include treatment regimens in which the agents are not necessarily administered by the same route of administration or at the same time.

The term "treating" or "treatment" as used herein comprises a treatment relieving, reducing or alleviating at least one symptom in a subject or effecting a delay of progression of a disease, condition and/or disorder. For example, treatment can be the diminishment of one or several symptoms of a disorder or complete eradication of a disorder. Within the meaning of the present invention, the term "treat" also denotes to arrest, delay the onset (i.e., the period prior to clinical manifestation of a disease) and/or reduce the risk of developing or worsening a disease.

The term "progression-free survival" as used herein comprises the length of time during and after the treatment of a disease, such as cancer, that a patient lives with the disease but it does not get worse. In a clinical trial, measuring the progression-free survival is one way to see how well a new treatment works. It is also called PFS.

The term "overall survival" as used herein comprises the length of time from either the date of diagnosis or the start of treatment for a disease, such as cancer, that patients diagnosed with the disease are still alive. In a clinical trial, measuring the overall survival is one way to see how well a new treatment works. It is also called OS.

The term "pharmaceutically effective amount" or "therapeutically effective amount" of a combination of therapeutic agents is an amount sufficient to provide an observable improvement over the baseline clinically observable signs and symptoms of the disease.

The term "synergistic effect" as used herein refers to action of two agents such as, for example, (a), and (b), or a pharmaceutically acceptable salt thereof, producing an effect, for example, promoting and/or enhancing an immune response in a subject, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

The term "subject" or "patient" as used herein includes animals, which are capable of promoting and/or enhancing an immune response and/or having an age related condition. Examples of subjects include mammals, e.g., humans, dogs, cows, horses, pigs, sheep, goats, cats, mice, rabbits, rats and transgenic non-human animals. In the preferred embodiment, the subject is a human, e.g., a human suffering from, at risk of suffering from, or potentially capable of suffering from cancer cachexia or an age related condition.

The term about" or "approximately" shall have the meaning of within 10%, more preferably within 5%, of a given value or range.

Herein after, the present invention is described in further detail and is exemplified.

The present invention is provided in its following aspects:
1. A combination comprising (a) ActRII receptor inhibitor and b) a chemotherapeutic agent.
2. A combination according to aspect 1 for simultaneous, separate or sequential use.
3. A combination according to aspect 1 or 2, wherein the a) ActRII receptor inhibitor, and b) a chemotherapeutic agent are in separate form.
4. A combination according to aspects 1-3 wherein a) is an anti-ActRII receptor antibody.
5. A combination according to aspects 1-4 wherein said anti-ActRII antibody is bimagrumab
6. A combination according to aspects 1-5 wherein b) is a platinum-containing anti-cancer agent.
7. A combination according to any of the preceding aspects for use as a medicament.
8. A combination according to aspect 1-6 comprising (a) ActRII receptor inhibitor and b) a chemotherapeutic agent for use in the treatment of cancer cachexia.
9. A combination according for use according to aspects 1-6 wherein the treatment of cancer cachexia is reduction of body weight loss.
10. An ActRII receptor inhibitor for use in treating cancer cachexia.
11. An ActRII receptor inhibitor for use according to aspect 11, wherein cancer cachexia is due to treatment with a chemotherapeutic agent.
12. An ActRII receptor inhibitor for use according to any aspect 10-12, wherein the wherein treating cancer cachexia is reducing body weight loss.
13. An ActRII receptor inhibitor for use according to aspects 10-12 in delaying time to progression of cancer in a patient.
14. An ActRII receptor inhibitor for use according to aspects 10-12 in delaying time to progression of cancer cachexia.
15. An ActRII receptor inhibitor for use according to aspects 10-12 in prolonging cancer survival.
16. An ActRII receptor inhibitor for use according to aspects 10-15, wherein the ActRII receptor inhibitor is an anti-ActRII receptor antibody.
17. An ActRII receptor inhibitor for use according to aspect 16 wherein the anti-ActRII receptor antibody is bimagrumab
18. An ActRII receptor inhibitor for use according to aspects 11-17, wherein the chemotherapeutic agent is a platinum-containing anti-cancer agent.
19. A combination comprising a) a myostatin antagonist and b) an mTOR inhibitor.
20. A combination according to aspect 19 wherein the myostatin antagonist is an ActRII receptor inhibitor
21. A combination according to aspect 20 wherein the ActRII receptor inhibitor is an anti-ActRII receptor antibody.
22. A combination according to aspect 21 wherein the anti-ActRII receptor antibody is bimagrumab.
23. A combination according to aspect 19-22 wherein the mTOR inhibitor is everolimus.
24. A combination according to aspects 19-23 for use as a medicament.
25. A combination according to aspects 19-23 for use in treating cancer cachexia.
26. A combination according to aspects 19-23 wherein treating cancer cachexia is preventing body weight loss.
27. A combination according to aspects 19-23 wherein treating cancer cachexia is maintaining body weight.
28. A combination according to aspects 19-23 wherein treating cancer cachexia is increasing body weight.

29. A combination according to aspects 1-9 or for use according to aspects 19-28 wherein the agents are in separate pharmaceutical compositions.
30. A combination according to any one of aspects 19-23 for use in the treatment of an age related condition.
31. A combination of aspect 30, wherein the age related condition is selected from the group consisting of sarcopenia, skin atrophy, muscle wasting, brain atrophy, atherosclerosis, arteriosclerosis, pulmonary emphysema, osteoporosis, osteoarthritis, high blood pressure, erectile dysfunction, dementia, Huntington's disease, Alzheimer's disease, cataracts, age-related macular degeneration, prostate cancer, stroke, diminished life expectancy, impaired kidney function, and age-related hearing loss, aging-related mobility disability (e.g., frailty), cognitive decline, age related dementia, memory impairment, tendon stiffness, heart dysfunction such as cardiac hypertrophy and systolic and diastolic dysfunction, immunosenescence, cancer, obesity, and diabetes.
32. A myostatin antagonist for use in delaying time to progression of cancer in a patient, wherein said patient is treated with a chemotherapeutic agent.
33. A myostatin antagonist for use according to aspect 30, wherein said chemotherapeutic agent is include platinum-containing anti-cancer drugs such as cisplatin or carboplatin, or a mTOR inhibitor such as everolimus.
34. A myostatin antagonist for use according to aspects 32-33 wherein said myostatin antagonist is an ActRII receptor inhibitor.
35. A myostatin antagonist for use according to aspect 34 wherein said ActRII receptor inhibitor is an anti-ActRII receptor antibody.
36. A myostatin antagonist for use according to aspect 35 wherein said anti-ActRII receptor antibody is bimagrumab.
37. A method of treating a subject having cancer cachexia which comprises administering to said subject an ActRII receptor inhibitor in quantity which is effective against said cancer cachexia.
38. The method of aspect 37, wherein cancer cachexia is due to treatment with a chemotherapeutic agent.
39. The method of aspect 38, wherein the chemotherapeutic agent is a platinum-containing anti-cancer agent.
40. The method of any aspects 37-39, wherein treating cancer cachexia is reducing body weight loss.
41. A method of delaying time to progression of cancer in a subject having cancer which comprises administering to said subject an ActRII receptor inhibitor in quantity which is effective in delaying time to progression of cancer.
42. A method of delaying time to progression of cancer in a subject having cancer cachexia which comprising administering to said subject an ActRII receptor inhibitor in quantity which is effective in delaying time to progression of cancer cachexia.
43. A method of prolonging cancer survival in a subject which comprising administering to said subject an ActRII receptor inhibitor in quantity which is effective in prolonging cancer survival.
44. The method according to aspects 37-44, wherein the ActRII receptor inhibitor is an anti-ActRII receptor antibody.
45. The method according to aspect 44, wherein the anti-ActRII receptor antibody is bimagrumab.
46. A method of treating a subject having cancer cachexia which comprises administering to said subject a myostatin antagonist and an mTOR inhibitor.
47. A method of treating a subject having an age-related condition which comprises administering to said subject a myostatin antagonist and an mTOR inhibitor.
48. The method of aspects 46-47, wherein the myostatin antagonist is an ActRII receptor inhibitor
49. The method according to aspect 48, wherein the ActRII receptor inhibitor is an anti-ActRII receptor antibody.
50. The method according to aspect 49, wherein the anti-ActRII receptor antibody is bimagrumab.
51. The method of aspects 46-50, wherein said mTOR inhibitor is everolimus.
52. The method of aspects 46-50, wherein the age related condition is selected from the group consisting of sarcopenia, skin atrophy, muscle wasting, brain atrophy, atherosclerosis, arteriosclerosis, pulmonary emphysema, osteoporosis, osteoarthritis, high blood pressure, erectile dysfunction, dementia, Huntington's disease, Alzheimer's disease, cataracts, age-related macular degeneration, prostate cancer, stroke, diminished life expectancy, impaired kidney function, and age-related hearing loss, aging-related mobility disability (e.g., frailty), cognitive decline, age related dementia, memory impairment, tendon stiffness, heart dysfunction such as cardiac hypertrophy and systolic and diastolic dysfunction, immunosenescence, cancer, obesity, and diabetes.
53. A method of treatment according to any preceding use or combination.

A preferred combination and uses thereof is bimagrumab and a platinum containing anti-cancer agent such as cisplatin.

Another preferred combination and uses thereof is bimagrumab and a mTOR inhibitor such as everolimus.

Further aspects comprise:

A combination comprising a) ActRII receptor inhibitor such as bimagrumab, and b) a P13K inhibitor.

A combination according to any of the preceding aspects comprising an ActRII receptor inhibitor such as bimagrumab and b) a VEGF receptor inhibitor.

A further specific aspect is a combination comprising a) ActRII receptor inhibitor such as bimagrumab, and b) a chemotherapeutic agent for use in improving progression-free survival.

Another further specific aspect is a combination comprising a) ActRII receptor inhibitor such as bimagrumab, and b) a chemotherapeutic agent for use in improving overall survival.

All aspects can be combined with each other within the scope of the present invention.

In further aspects, the invention provides pharmaceutical compositions separately comprising a quantity, which is jointly therapeutically effective at treating cancer cachexia, uses thereof or methods of treating cancer cachexia using such pharmaceutical compositions, for delaying time to progression of cancer/cancer cachexia, for prolonging cancer survival, improving progression-free survival, or overall survival and for treating an age-related condition, of a combination partner (a) and a combination partner (b) which are administered concurrently but separately, or administered sequentially.

Bimagrumab

The manufacture of bimagrumab has been described in WO2010/125003.

Bimagrumab comprises an antigen binding site comprising at least one immunoglobulin heavy chain variable domain ($V_H$) which comprises in sequence hypervariable regions CDR1 of SEQ ID N°1, CDR2 of SEQ ID N°2 and CDR3 of SEQ ID N°3.

The use of antibodies having 1, 2 or 3 residues changed from any of the sequences of CDR1, CDR2 and/or CDR3 of the heavy chain is also comprised within the scope of the invention.

Bimagrumab also comprises antigen binding site comprising at least one immunoglobulin light chain variable domain ($V_L$) which comprises in sequence hypervariable regions CDR1 of SEQ ID N°4, CDR2 of SEQ ID N°5 and CDR3 of SEQ ID N°6 or CDR equivalents thereof.

The use of antibodies having 1, 2 or 3 residues changed from any of the sequences of CDR1, CDR2 and/or CDR3 of the light chain is also comprised within the scope of the invention.

Bimagrumab also comprises a light chain of SEQ ID N°7 or SEQ ID N°8 and a heavy chain of SEQ ID N°9.

According to the invention the use of antibodies having 95% identity with the light chain and/or the heavy chain are also comprised.

SEQUENCE LISTING for BIMAGRUMAB

<130> PAT057144-US-PSP

<160> 9

<170> PatentIn version 3.5

<210> 1

<211> 10

<212> PRT

<213> Artificial

<220>

<223> Heavy chain CDR1

<400> 1

Gly Tyr Thr Phe Thr Ser Ser Tyr Ile Asn
1               5                   10

<210> 2

<211> 17

<212> PRT

<213> Artificial

<220>

<223> Heavy chain CDR2

<400> 2

Thr Ile Asn Pro Val Ser Gly Ser Thr Ser Tyr Ala Gln Lys Phe Gln
1               5                   10                  15
Gly

<210> 3

<211> 6

<212> PRT

<213> Artifical

<220>

<223> Heavy chain CDR3

<400> 3

Gly Gly Trp Phe Asp Tyr
1               5

<210> 4

<211> 14

<212> PRT

<213> Artificial

SEQUENCE LISTING for BIMAGRUMAB

<220>

<223> Light chain CDR1

<400> 4

Thr Gly Thr Ser Ser Asp Val Gly Ser Tyr Asn Tyr Val Asn
1               5                   10

<210> 5

<211> 11

<212> PRT

<213> Artifical

<220>

<223> Light chain CDR2

<400> 5

Leu Met Ile Tyr Gly Val Ser Lys Arg Pro Ser
1               5                   10

<210> 6

<211> 10

<212> PRT

<213> Artificial

<220>

<223> Light chain CDR3

<400> 6

Gly Thr Phe Ala Gly Gly Ser Tyr Tyr Gly
1               5                   10

<210> 7

<211> 217

<212> PRT

<213> Artificial

<220>

<223> light chain

<400> 7

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
                20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
            100                 105                 110

-continued

| SEQUENCE LISTING for BIMAGRUMAB |
|---|

Gln Pro Lys Ala Ala Pro Ser Val Thr Leu Phe Pro Pro Ser Ser Glu
    115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
            165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
   210                 215

<210> 8

<211> 217

<212> PRT

<213> Artificial

<220>

<223> light chain

<400> 8

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
            85                  90                  95

Ser Tyr Tyr Gly Val Phe Gly Gly Gly Thr Lys Leu Thr Val Leu Gly
        100                 105                 110

Gln Pro Lys Ala Ala Pro Ser Val Thr Leu Phe Pro Pro Ser Ser Glu
    115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
            165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
   210                 215

SEQUENCE LISTING for BIMAGRUMAB

<210> 9

<211> 445

<212> PRT

<213> Artificial

<220>

<223> heavy chain

<400> 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Thr Ile Asn Pro Val Ser Gly Ser Thr Ser Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

-continued

SEQUENCE LISTING for BIMAGRUMAB

```
Ala Lys Gly Gln Pro Arg Glu Pro Gln Val Tyr Thr Leu Pro Pro Ser
    340                 345                 350

Arg Glu Glu Met Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
    405                 410                 415

Gln Gly Asn Val Phe Ser Cys Ser Val Met His Glu Ala Leu His Asn
    420                 425                 430

His Tyr Thr Gln Lys Ser Leu Ser Leu Ser Pro Gly Lys
    435                 440                 445

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
    325                 330                 335

Pro Arg Glu Pro Gln Val Tyr Thr Leu Pro Pro Ser Arg Glu Glu Met
    340                 345                 350

Thr Lys Asn Gln Val Ser Leu Thr Cys Leu Val Lys Gly Phe Tyr Pro
    355                 360                 365

Ser Asp Ile Ala Val Glu Trp Glu Ser Asn Gly Gln Pro Glu Asn Asn
    370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
    405                 410                 415

Phe Ser Cys Ser Val Met His Glu Ala Leu His Asn His Tyr Thr Gln
    420                 425                 430

Lys Ser Leu Ser Leu Ser Pro Gly Lys
    435                 440
```

Cachexia or wasting syndrome is loss of weight, muscle atrophy, fatigue, weakness, and significant loss of appetite in someone who is not actively trying to lose weight. The formal definition of cachexia is the loss of body mass (weight) that cannot be reversed nutritionally: even if the affected patient eats more calories, lean body mass will be lost, indicating a primary pathology is in place.

Cachexia is seen in patients with cancer, AIDS chronic obstructive lung disease, multiple sclerosis, congestive heart failure, tuberculosis, familial amyloid polyneuropathy, gadolinium poisoning, mercury poisoning (acrodynia) and hormonal deficiency.

It is a positive risk factor for death, meaning if the patient has cachexia, the chance of death from the underlying condition is increased dramatically. It can be a sign of various underlying disorders; when a patient presents with cachexia, a doctor will generally consider the possibility of cancer, metabolic acidosis (from decreased protein synthesis and increased protein catabolism), certain infectious diseases (e.g., tuberculosis, AIDS), chronic pancreatitis, and some autoimmune disorders, or addiction to amphetamine. Cachexia physically weakens patients to a state of immobility stemming from loss of appetite, asthenia, and anemia, and response to standard treatment is usually poor. Cachexia includes sarcopenia as a part of its pathology.

Cancer Cachexia:

Cancer cachexia is a multifactorial syndrome that is defined by an ongoing loss of skeletal muscle mass (with or without loss of fat mass) that cannot be fully reversed by conventional nutritional support and that leads to progressive functional impairment.

Chemotherapeutic Agents:

Chemotherapeutic agents include platinum-containing anti-cancer drugs (e.g. cisplatin, carboplatin), PI3K/mTOR inhibitor, everolimus, PI3K inhibitors and VEGFR inhibitors. In a broader sense referring as "chemotherapy", those include alkylating agents (e.g. cyclophosphamide, temozolomide), platinum-containing agents, anti-metabolites (e.g. 5-fluorouracil, methotrexate, hydroxyurea, cytarabine, gemcitabine), topoisomerase inhibitor (e.g. doxorubicin, irinotecan), microtubule polymerizing/depolymerizing agent (e.g. vinblastine, vincristine, paclitaxel, docetaxel), endocrine agent (e.g. bicalutamide, leuprorelin, tamoxifen, letrozole), and more recently molecular targeted agents (e.g. kinase inhibitors, antibodies).

mTOR Inhibitors:

As used herein, the term "mTOR inhibitor" refers to a compound or ligand, or a pharmaceutically acceptable salt thereof, which inhibits the mTOR kinase in a cell. In an embodiment an mTOR inhibitor is an allosteric inhibitor. In an embodiment an mTOR inhibitor is a catalytic inhibitor.

Allosteric mTOR inhibitors include the neutral tricyclic compound rapamycin (sirolimus), rapamycin-related compounds, that is compounds having structural and functional similarity to rapamycin including, e.g., rapamycin derivatives, rapamycin analogs (also referred to as rapalogs) and other macrolide compounds that inhibit mTOR activity.

Rapamycin is a known macrolide antibiotic produced by Streptomyces hygroscopicus having the structure shown in Formula A.

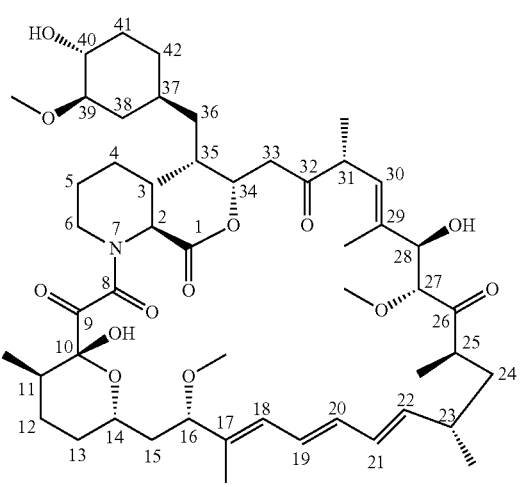

See, e.g., McAlpine, J. B., et al., J. Antibiotics (1991) 44: 688; Schreiber, S. L., et al., J. Am. Chem. Soc. (1991) 113: 7433; U.S. Pat. No. 3,929,992. There are various numbering schemes proposed for rapamycin. To avoid confusion, when specific rapamycin analogs are named herein, the names are given with reference to rapamycin using the numbering scheme of formula A.

Rapamycin analogs useful in the invention are, for example, O-substituted analogs in which the hydroxyl group on the cyclohexyl ring of rapamycin is replaced by $OR_1$ in which $R_1$ is hydroxyalkyl, hydroxyalkoxyalkyl, acylaminoalkyl, or aminoalkyl; e.g. RAD001, also known as, everolimus as described in U.S. Pat. No. 5,665,772 and WO94/09010 the contents of which are incorporated by reference. Other suitable rapamycin analogs include those substituted at the 26- or 28-position. The rapamycin analog may be an epimer of an analog mentioned above, particularly an epimer of an analog substituted in position 40, 28 or 26, and may optionally be further hydrogenated, e.g. as described in U.S. Pat. No. 6,015,815, WO95/14023 and WO99/15530 the contents of which are incorporated by reference, e.g. ABT578 also known as zotarolimus or a rapamycin analog described in U.S. Pat. No. 7,091,213, WO98/02441 and WO01/14387 the contents of which are incorporated by reference, e.g. AP23573 also known as ridaforolimus.

Examples of rapamycin analogs suitable for use in the present invention from U.S. Pat. No. 5,665,772 include, but are not limited to, 40-O-benzyl-rapamycin, 40-O-(4'-hydroxymethyl)benzyl-rapamycin, 40-O-[4'-(1,2-dihydroxyethyl)]benzyl-rapamycin, 40-O-allyl-rapamycin, 40-O-[3'-(2 2-dimethyl-1,3-dioxolan-4(S)-yl)-prop-2'-en-1'-yl] rapamycin, (2'E,4'S)-40-O-(4',5'-dihydroxpent-2'-en-1'-yl)-rapamycin, 40-O-(2-hydroxy)ethoxycarbonylmethyl-rapamycin, 40-O-(2-hydroxy)ethyl-rapamycin, 40-O-(3-hydroxy)propyl-rapamycin, 40-O-(6-hydroxy)hexyl-rapamycin, 40-O-[2-(2-hydroxy)ethoxy]ethyl-rapamycin, 40-O-[(3S)-2,2-dimethyldioxolan-3-yl]methyl-rapamycin, 40-O-[(2S)-2,3-dihydroxyprop-1-yl]rapamycin, 40-O-(2-acetoxy)ethyl-rapamycin, 40-O-(2-n icotinoyloxy)ethyl-rapamycin, 40-O-[2-(N-morpholino)acetoxy]ethyl-rapamycin, 40-O-(2-N-imidazolylacetwry)ethyl-rapamycin, 40-O-[2-(N-methyl-N'-piperazinyl)acetoxy]ethyl-rapamycin, 39-O-desmethyl-39,40-O,O-ethylene-rapamycin, (26R)-26-dihydro-40-O-(2-hydroxy)ethyl-rapamycin, 40-O-(2-aminoethyl)-rapamycin, 40-O-(2-acetaminoethyl)-rapamycin, 40-O-(2-nicotinamidoethyl)-rapamycin, 40-O-(2-(N-methyl-imidazo-2'-ylcarbethoxamido)ethyl)-rapamycin, 40-O-(2-ethoxycarbonylaminoethyl)-rapamycin, 40-O-(2-tolylsulfonamidoethyl)-rapamycin and 40-O-[2-(4',5'-dicarboethoxy-1',2',3'-triazol-1'-yl)-ethyl]-rapamycin.

Other rapamycin analogs useful in the present invention are analogs where the hydroxyl group on the cyclohexyl ring of rapamycin and/or the hydroxy group at the 28 position is replaced with an hydroxyester group are known, for example, rapamycin analogs found in U.S. RE44,768, e.g. temsirolimus.

Other rapamycin analogs useful in the present invention include those wherein the methoxy group at the 16 position is replaced with another substituent, preferably (optionally hydroxy-substituted) alkynyloxy, benzyl, orthomethoxybenzyl or chlorobenzyl and/or wherein the mexthoxy group at the 39 position is deleted together with the 39 carbon so that the cyclohexyl ring of rapamycin becomes a cyclopentyl ring lacking the 39 position methyoxy group; e.g. as described in WO95/16691 and WO96/41807 the contents of which are incorporated by reference. The analogs can be further modified such that the hydroxy at the 40-position of rapamycin is alkylated and/or the 32-carbonyl is reduced.

Rapamycin analogs from WO95/16691 include, but are not limited to, 16-demthoxy-16-(pent-2-ynyl)oxy-rapamycin, 16-demthoxy-16-(but-2-ynyl)oxy-rapamycin, 16-demthoxy-16-(propargyl)oxy-rapamycin, 16-demethoxy-16-(4-hydroxy-but-2-ynyl)oxy-rapamycin, 16-demthoxy-16-benzyloxy-40-O-(2-hydroxyethyl)-rapamycin, 16-demthoxy-16-benzyloxy-rapamycin, 16-demethoxy-16-ortho-methoxybenzyl-rapamycin, 16-demethoxy-40-O-(2-methoxyethyl)-16-pent-2-ynyl)oxy-rapamycin, 39-demethoxy-40-desoxy-39-formyl-42-nor-rapamycin, 39-demethoxy-40-desoxy-39-hydroxymethyl-42-nor-rapamycin, 39-demethoxy-40-desoxy-39-carboxy-42-nor-rapamycin, 39-demethoxy-40-desoxy-39-(4-methyl-piperazin-1-yl)carbonyl-42-nor-rapamycin, 39-demethoxy-40-desoxy-39-(morpholin-4-yl)carbonyl-42-nor-rapamycin, 39-demethoxy-40-desoxy-39-[N-methyl, N-(2-pyridin-2-ylethyl)]carbamoyl-42-nor-rapamycin and 39-demethoxy-40-desoxy-39-(p-toluenesulfonylhydrazonomethyl)-42-nor-rapamycin.

Rapamycin analogs from WO96/41807 include, but are not limited to, 32-deoxo-rapamycin, 16-O-pent-2-ynyl-32-deoxo-rapamycin, 16-O-pent-2-ynyl-32-deoxo-40-O-(2-hydroxy-ethyl)-rapamycin, 16-O-pent-2-ynyl-32-(S)-dihydro-40-O-(2-hydroxyethyl)-rapamycin, 32(S)-dihydro-40-O-(2-methoxy)ethyl-rapamycin and 32(S)-dihydro-40-O-(2-hydroxyethyl)-rapamycin.

Another suitable rapamycin analog is umirolimus as described in US2005/0101624 the contents of which are incorporated by reference.

In mammalian cells, the target of rapamycin (mTOR) kinase exists as a multiprotein complex described as the mTORC1 complex or mTORC2 complex, which senses the availability of nutrients and energy and integrates inputs from growth factors and stress signaling. The mTORC1 complex is sensitive to allosteric mTOR inhibitors such as rapamycin, is composed of mTOR, GβL, and regulatory associated proteins of mTOR (raptor), and binds to the peptidyl-prolyl isomerase FKBP12 protein (a FK506-binding protein 1A, 12 kDa). In contrast, the mTORC2 complex is composed of mTOR, GβL, and rapamycin-insensitive companion proteins of mTOR (rictor), and does not bind to the FKBP12 protein in vitro.

The mTORC1 complex has been shown to be involved in protein translational control, operating as a growth factor and nutrient sensitive apparatus for growth and proliferation regulation. mTORC1 regulates protein translation via two key downstream substrates: P70 S6 kinase, which in turn phosphorylates ribosomal protein P70 S6, and eukaryotic translation initiation factor 4E binding protein 1 (4EBP1), which plays a key role in modulating eIF4E regulated cap-dependent translation. The mTORC1 complex regulates cell growth in response to the energy and nutrient homeostasis of the cell, and the deregulation of mTORC1 is common in a wide variety of human cancers. The function of mTORC2 involves the regulation of cell survival via phosphorylation of Akt and the modulation of actin cytoskeleton dynamics.

The mTORC1 complex is sensitive to allosteric mTOR inhibitors such as rapamycin and derivatives in large part due to rapamycin's mode of action, which involves the formation of an intracellular complex with the FKBP12 and binding to the FKBP12-rapamycin binding (FRB) domain of mTOR. This results in a conformational change in mTORC1 which is believed to alter and weaken the interaction with its scaffolding protein raptor, in turn impeding substrates such as P70 S6K1 from accessing mTOR and being phosphorylated. Rapamycin and rapalogues such as RAD001 have gained clinical relevance by inhibiting hyperactivation of mTOR associated with both benign and malignant proliferation disorders. RAD001, otherwise known as everolimus (Afinitor®), has the chemical name (1R,9S,12S,15R,16E,18R,19R,21R,23S,24E,26E,28E,30S,32S,35R)-1,18-dihydroxy-12-{(1R)-2-[(1S,3R,4R)-4-(2-hydroxyethoxy)-3-methoxycyclohexyl]-1-methylethyl}-19,30-dimethoxy-15,17,21,23,29,35-hexamethyl-11,36-dioxa-4-aza-tricyclo[30.3.1.04,9]hexatriaconta-16,24,26,28-tetraene-2,3,10,14,20-pentaone and the following chemical structure

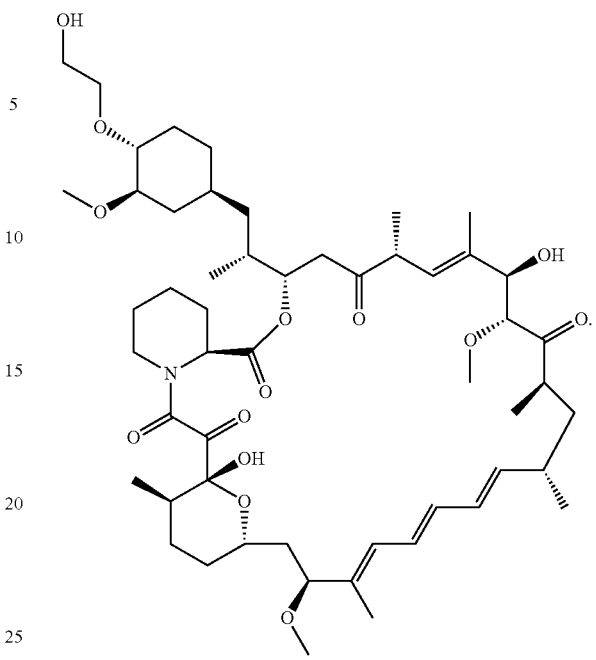

Everolimus is an FDA approved drug for the treatment of advanced kidney cancer and is being investigated in several other phase III clinical trials in oncology. Preclinical studies have shown that Everolimus is able to inhibit the proliferation of a wide variety of tumor cell lines both in vitro and in vivo, presumably through the suppression of rapamycin sensitive mTORC1 function. Everolimus, as a derivative of rapamycin, is an allosteric mTOR inhibitor that is highly potent at inhibiting part of the mTORC1 function, namely P70 S6 kinase (P70 S6K) and the downstream P70 S6K substrate P70 S6. Allosteric mTOR inhibitors like everolimus (and other rapamycin analogs) have little or no effect at inhibiting the mTORC2 pathway, or its resulting activation of Akt signaling. Further examples of allosteric mTOR inhibitors include sirolimus (rapamycin, AY-22989), 40-[3-hydroxy-2-(hydroxymethyl)-2-methylpropanoate]-rapamycin (also called temsirolimus or CCI-779) and ridaforolimus (AP-23573/MK-8669). Other examples of allosteric mTOR inhibtors include zotarolimus (ABT578) and umirolimus.

Alternatively or additionally, catalytic, ATP-competitive mTOR inhibitors have been found to target the mTOR kinase domain directly and target both mTORC1 and mTORC2. These are also more complete inhibitors of mTORC1 than such allosteric mTOR inhibitors as rapamycin, because they modulate rapamycin-resistant mTORC1 outputs such as 4EBP1-T37/46 phosphorylation and cap-dependent translation.

The combination of bimagrumab and mTOR inhibitors such as everolimus may be particularly effective for the treatment of aging-related muscle dysfunction because bimagrumab increases muscle mass and everolimus improves muscle quality. Bimagrumab improves muscle mass by inhibiting the myostatin/activin pathway. Everolimus improves muscle function by inhibiting the mTOR pathway which is over-active in old muscle (unpublished internal data that we could add). Inhibition of mTOR may improve muscle function by enhancing mitochondrial function, decreasing inflammation and increasing autophagy. Improving muscle mass and function with the combination of bimagrumab and mTOR inhibitors such as everolimus is likely to have therapeutic benefit in sarcopenia and heart failure. In addition, improving muscle mass and function may have therapeutic benefit in diabetes mellitus by increasing glucose uptake in muscle. Increased mTOR activity has also been demonstrated in muscle biopsies obtained from older healthy subjects (ages 60-84) as compared to younger healthy subjects (ages 18-40) (Markofski M et al., Exp Geront, 2015)

EXAMPLES

Hereinafter, the present invention is described in more details and specifically with reference to the examples, which however are not intended to limit the present invention.

Material and methods

Materials Bimagrumab is a human, IgG1 Leu234Ala/Leu235Ala monoclonal antibody directed against ActRII. CDD866, a murinized version of bimagrumab, where the human Fc region of the antibody has been replaced by a mouse Fc.CDD866 was produced in CHO cells at Novartis Pharma AG (Basel, Switzerland). Cisplatin (cis-diamminedichloro-platinum(II)) was purchased from Sigma Aldrich (catalog number 479306). Everolimus was synthesized at Novartis Pharma AG.

Animal Experiments

Adult male Balb/cJRj mice at the age of 11 to 12 weeks were purchased from Janvier Laboratories (Le Genest St Isle, France). Mice were acclimated to the facility for 7 days. Animals were housed in groups of 5 or less animals at 25° C. with a 12:12 h light-dark cycle. They were fed a standard laboratory diet containing 18.2% protein and 3.0% fat with an energy content of 15.8 MJ/kg (NAFAG 3890, Kliba, Basel, Switzerland). Food and water were provided ad libitum.

Mouse colon cancer cell line CT-26 was cultured in RPMI 1640 medium supplemented with 10% heat inactivated fetal bovine serum and antibiotic-antimycotic solution at 37° C. with 5% $CO_2$. CT-26 cells were harvested by treatment with Accutase® (PAA Laboratories GmbH, Pasching, Austria) and suspended in a solution containing 50% PBS and 50% BD Matrigel™ Matrix without phenol red (catalog number 356237, BD Biosciences, Bedford, Mass., USA). A 0.1 mL of cell suspension containing $3\times10^5$ cells was inoculated subcutaneously into the left flank of mice. When tumors were palpable, mice bearing tumors with acceptable morphology and size were randomized to produce groups balanced with respect to mean and range of tumor sizes and body weight. Treatments were initiated on the day of randomization. Therapeutic intervention study was conducted to evaluate the effect of CDD866, either alone or in combination with anti-cancer agents. CDD866 was administered at 20 mg/kg s.c., once or twice weekly in a volume of 5 mL/kg. Cisplatin was administered at 1 mg/kg i.p. twice a week. Everolimus was administered at 5 mg/kg p.o. once daily. In the combination groups, cisplatin or everolimus treatment was combined with once or twice weekly subcutaneous treatment of CDD866, respectively. Body weight and tumor volume were measured 2 to 3 times per week. At the end of the experiment, the mice were euthanized with $CO_2$, and tumor, tibialis anterior, gastrocnemius-soleus-plantaris complex, quadriceps were collected and weighed.

Time-to-progression study was performed as a follow-up to assess if the combination of CDD866 and cisplatin or everolimus slows progression of cancer cachexia to the interruption criteria which was defined by body weight loss reaching to 20% or tumor volume exceeding 1,500 $mm^3$.

The treatment regimen was the same as used in the therapeutic intervention study. Body weight and tumor volume were measured 2 to 3 times per week in the first 2 weeks and then every day until the end of experiment. The mice were euthanized with $CO_2$, when body weight loss was close to 20% or tumor volume exceeded 1,500 $mm^3$.

Protein Analysis

Lysis buffer consisting of extraction reagent (Phosphosafe; Novagen Inc., Madison, Wis., USA) supplemented with 1% protease inhibitor cocktail (calbiochem# 539131) and 0.2% SDS was added. Precellys Homogenates (FastPrep-Machine FP20), were separated by centrifugation for 20 minutes at 4° C. (14,000 rpm). Supernatants were collected and protein contents measured a commercial kit for protein determination (BCA Kit; Thermo Scientific). Samples were diluted in SDS-PAGE sample buffer and denatured for 10 minutes at 70° C. Equal amounts of protein were loaded per lane of 4 to 12% and 8% polyacrylamide gel (NuPAGE Bis-Tris gel; Invitrogen Corp., Carlsbad, Calif., USA), separated by electrophoresis, and then transferred onto nitrocellulose membranes. Membranes were blocked in TBS with 0.1% Tween and 5% w/v non-fat milk powder. Primary antibodies phospho-SMAD3 (Millipore #04 1042 diluted 1:1000) and a-Tubulin (Sigma T6199 Diluted 1:5000) were incubated in TBS with 0.1% Tween 20 and 5% w/v non-fat milk powder and secondary antibodies in TBS with 0.1% Tween 20, 0.05% SDS and 5% non-fat milk. Immunoreactivity was detected by SuperSignal West Femto Maximum Sensitivity Substrate (Thermo Scientific) and exposed to film or acquired by FusionSpectra. Quantitative determination of mTOR and IL-6 was performed using an assay kit from MesoScale Discovery using a MesoScale Discovery reader according to the manufacturers instruction.

Statistical Analysis

Values are expressed as mean±SEM. Statistical analysis was carried out using Sidak's multiple comparison test following analysis of variance to compare the treatment groups to the control groups (non-tumor and tumor-bearing), anti-cancer agent alone (cisplatin or everolimus) or CDD866 alone in the therapeutic intervention study, and Dunn's multiple comparisons test for time-to-progression study. Differences were considered to be significant when the probability value was <0.05. Statistical analyses were performed by GraphPad Prism (GraphPad Software, Inc., La Jolla, Calif., USA). Body weight was expressed as % change from day 0 as the start of treatment. Tumor volumes in cubic mm were calculated according to the formula (length× $width^2$)/2. Muscle weight was normalized to the body weight on the day of cell inoculation (initial body weight) and then expressed as % change from the non-tumor control group.

Example 1

Bimagrumab Prevents Cisplatin-Induced Body Weight Loss

Extensive body weight loss has emerged as a key determinant of cancer-related death. Thus longitudinally body weight development was monitored (FIGS. 1A and B). Ten days after starting the treatment, tumor-bearing animals receiving cisplatin as a mono-therapy had lost 20% of their initial body weight (FIGS. 1B and C). By contrast, vehicle-treated, tumor-bearing animals experienced a body weight decrease of 10%, while animals treated with CDD866 alone or in combination with cisplatin exhibited moderate body weight losses of only 3 and 5%, respectively (FIGS. 1B and C). In healthy control animals, cisplatin did not affect body weight and CDD866 administration resulted in a marked body weight gain in the absence and presence of cisplatin (FIGS. 1A and C). These data demonstrate that cisplatin, at an effective anti-tumor dose (cf. FIG. 1E), indeed precipitated body weight loss in cachectic animals and that CDD866 significantly reduced chemotherapy-induced wasting.

Major concerns to be addressed in this study were potential drug-drug interactions that might reduce the efficacy of chemotherapy and impacts of CDD866 on tumor growth promotion. At treatment initiation, the average tumor volume was ≥260 mm³ (FIG. 1D). CDD866 neither accelerated tumor progression (FIGS. 1D and E), nor did it impair the anti-tumor effect of cisplatin (FIGS. 1D and E). Thus, CDD866 is efficacious in reducing chemotherapy-mediated body weight loss in cancer cachexia without interfering with the anti-tumor effect of cisplatin.

Example 2

Bimagrumab Antagonizes Cisplatin-Induced Muscle Wasting

Figure 2:
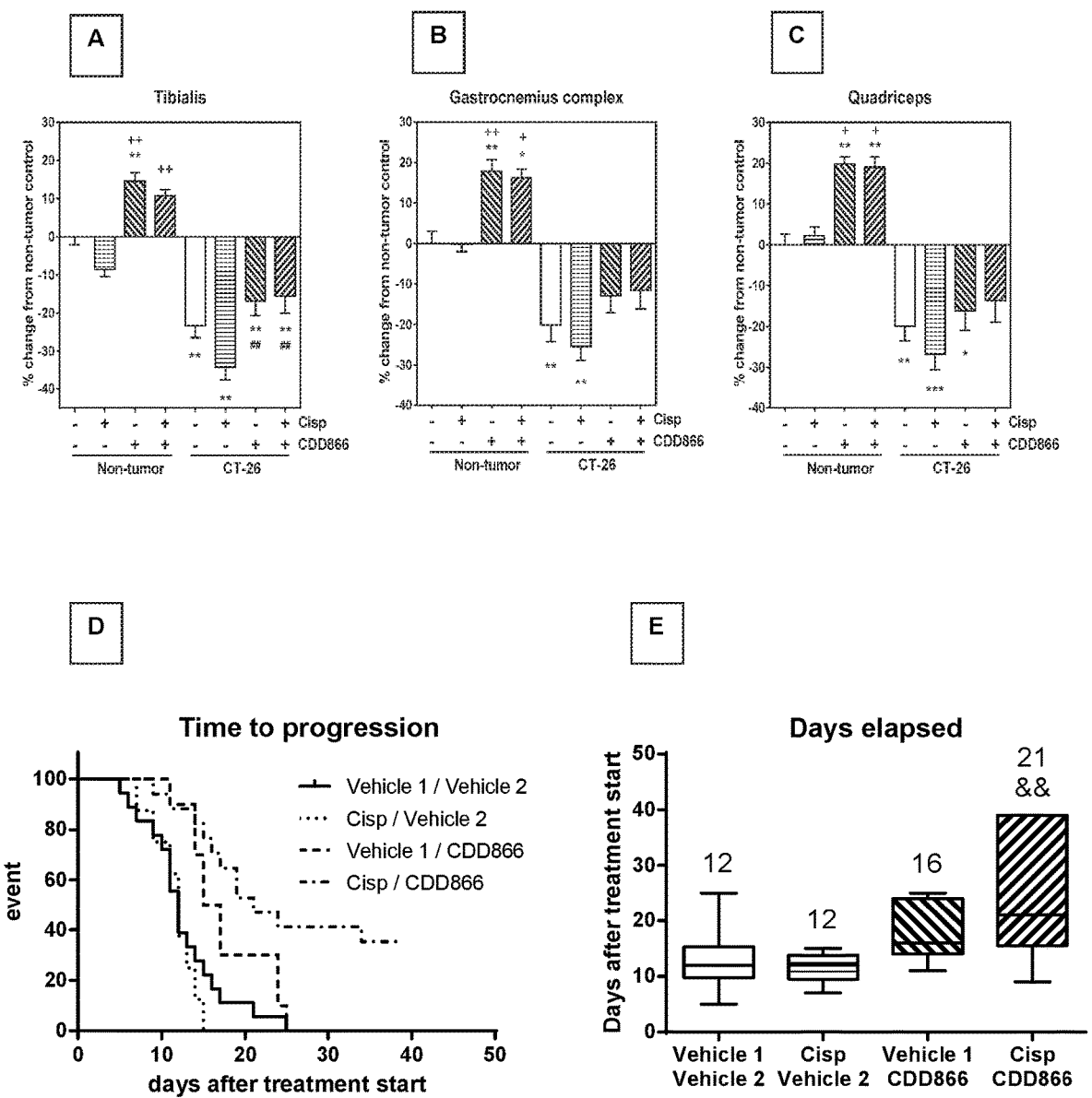
FIG. 2: The effects of cisplatin and CDD866 on muscle weight and time-to-progression in CT-26 mouse colon cancer-induced cachexia, either alone or in combination. Values are expressed as means±SEM (n=10). Percent changes of muscle weight, normalized to initial body weight on day 0, were calculated in comparison to Non-tumor control (A, B, C); *: P<0.05, **: P<0.01 versus Non-tumor control; $^{\&}$: P<0.05, $^{\&\&}$: P<0.01 versus CT-26 control; $^{++}$: P<0.01 versus Non-tumor cisplatin; $^{\times\times}$: P<0.01 versus Non-tumor CDD866; $^{\#\#}$: P<0.01 versus CT-26 cisplatin; $^{\$}$: P<0.05, $^{\$\$}$: P<0.01 versus CT-26 CDD866 by Sidak's multiple comparison test following ANOVA. Time-to-progression expressed by % event defined by interruption criteria (D); median days elapsed before reaching an interruption criterion (E), expressed by box and whiskers with min to max (n=10); $^{\&}$: P<0.05, $^{\&\&}$: P<0.01 versus CT-26 control (Vehicle 1/Vehicle 2) by Dunn's multiple comparison test following ANOVA.

Given the positive effect of CDD866 on body weight, we next determined the impact of the various interventions on individual skeletal muscles. In gastrocnemius, cisplatin provoked a muscle weight loss of 25%. CDD866 treatment tended to reduce muscle weight loss to 13% and this protective effect was preserved in the presence of cisplatin (12%) (FIG. 2B). A similar level of protection was observed in quadriceps muscle (FIG. 2C). Tibialis anterior benefited most from CDD866 treatment. In tibialis anterior, cisplatin-treated animals experienced a muscle wasting of 34% and co-administration of CDD866 reduced muscle loss significantly to 16% (FIG. 2A).

Example 3

Bimagrumab in Combination with Cisplatin Delays Time to Progression in Cancer Cachexia Extensive tumor growth and subsequent body weight loss are important predictors of mortality in cancer patients. We therefore wanted to evaluate whether the combination of CDD866 and cisplatin has an impact on the length of survival. For ethical reason we abstained from classical survival studies. Instead, each mouse was individually euthanized when experiencing either a body weight loss exceeding 20% of initial body weight, or reaching a tumor volume of 1,500 mm³, determined as time-to-progression.

On average, animals receiving vehicle or cisplatin had to be sacrificed after 12 and 12 days, respectively (FIGS. 2D and E). CDD866 treated animals had to be euthanized after 16 days, which corroborates previous findings that CDD866 treatment reduced body weight loss, but did not promote tumor growth. The combined treatment of CDD866 and cisplatin was superior to any other intervention tested. Indeed, combination treatment extended time-to-progression up to 21 days (FIG. 2E). Monitoring was stopped after 39 days with 35% of animals in the combination group still not having reached one of the defined interruption criteria (FIG. 2D).

Combination with Cisplatin

Despite substantial tumor growth inhibition, cisplatin accelerated body weight loss in cachectic animals, likely due to the high toxicity of the anti-cancer agent. CDD866 fully prevented cisplatin-mediated body weight loss demonstrating that ActRII inhibition remained efficacious in the presence of cisplatin. Cisplatin treatment alone and also in combination with CDD866 reduced CT-26 tumor weight to similar levels, which underlines that the anti-cancer effect of cisplatin was not negatively affected by CDD866.

Consistently, cisplatin treatment did not improve CT-26 tumor-induced skeletal muscle wasting, but rather tended to exacerbate skeletal muscle loss. In contrast, administration of CDD866 alone or in combination with cisplatin protected from skeletal muscle weight loss compared to animals receiving only cisplatin, corroborating further that ActRII inhibition remains fully efficacious under cisplatin treatment. These results thus demonstrate that CDD866 in combination with cisplatin counters muscle wasting in cachectic animals when compared to cisplatin treatment alone. Noteworthy, CDD866 was administered only once per week and mice received only two injections throughout the entire study (apart from the survival studies). Since the release of Activin by cancer tissues[17] might potentially compete with ActRII inhibition by CDD866, a higher dosing or frequency of dosing of CDD866 might be required in cancer cachexia to elicit more pronounced or maximal responses. Indeed, stronger muscle wasting sparing was noticed with CDD866 alone in the combination study with everolimus under a more frequent dosing regimen.

Cancer patients with low muscle mass are at increased risk for treatment-related toxicities from chemotherapy and show increased overall mortality[18]. Consistently, CDD866 significantly delayed disease progression largely by increasing muscle mass. Time-to-progression in cancer cachexia was even further retarded by concomitant therapy with CDD866 and cisplatin, which simultaneously countered muscle wasting and inhibited tumor growth Example 4

Bimagrumab and Everolimus Prevent Cancer Cachexia in an Additive Way

In the next step, everolimus, a molecular-targeted agent against mammalian Target of Rapamycin (mTOR), was selected as a combination partner because mTOR is known to play a pivotal role in cell growth and proliferation. In addition, treatment frequency for CDD866 was increased to twice weekly to ensure significant anti-cachectic effect when administered as single agent, and the combination of everolimus and CDD866 was evaluated in non-tumor mice as well as tumor-bearing cachectic mice.

Figure 3:
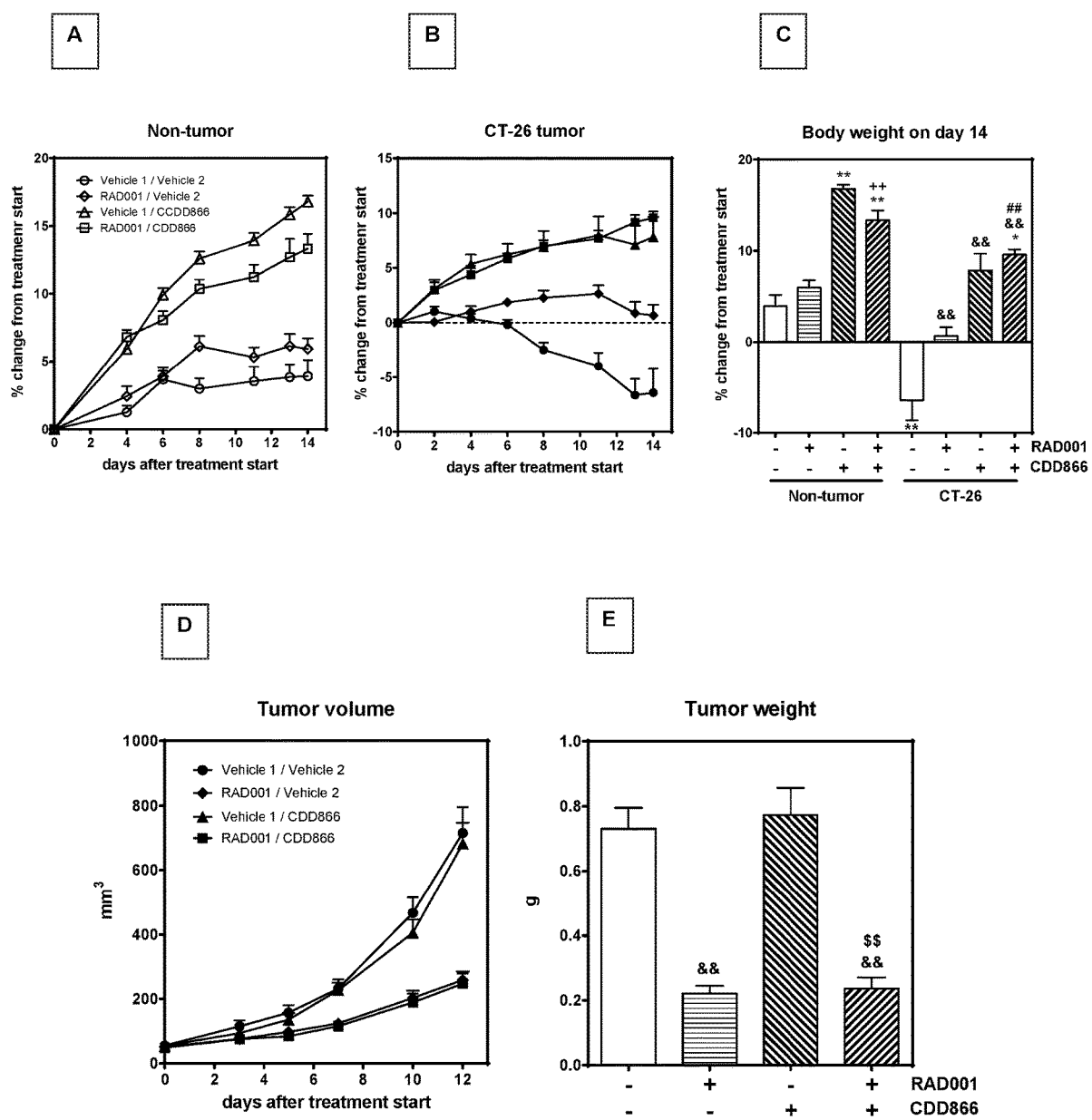
FIG. 3: The effects of everolimus and CDD866 on body weight (A, B, C), tumor volume (D) and weight (E) in CT-26 mouse colon cancer-induced cachexia, either alone or in combination. Values are expressed as means±SEM (n=10). Percent changes of body weight were calculated in comparison to treatment start on day 0; *: P<0.05, **: P<0.01 versus Non-tumor control; $^{\&\&}$: P<0.01 versus CT-26 control; $^{++}$: P<0.01 versus Non-tumor everolimus; $^{\#\#}$: P<0.01 versus CT-26 everolimus by Sidak's multiple comparison test following ANOVA.

In the non-tumor bearing group, body weight gain was not affected significantly by everolimus treatment. In contrast, body weight gain increased significantly with CDD866 treatment as expected (FIGS. 3A and C). The body weight increase was slightly slower in the combination group (FIGS. 3A and C), but still significantly different from everolimus alone, and not significantly different from CDD866 alone up to the termination on day 14. In the CT-26 group, body weight was significantly decreased in the tumor-bearing control group on day 14 when compared to the non-tumor control group (FIGS. 3B and C). CT-26-induced loss in body weight was completely prevented by everolimus, CDD866 and the combination of everolimus and CDD866. The effect of CDD866 on body weight was maintained in the presence of everolimus.

Everolimus slowed CT-26 tumor growth, and the anti-tumor effect was maintained in the presence of CDD866 (FIG. 3D). CT-26 tumor weight was significantly reduced with everolimus treatment alone or in combination with CDD866. There was no significant effect of CDD866 treatment on CT-26 tumor weight.

Figure 4:
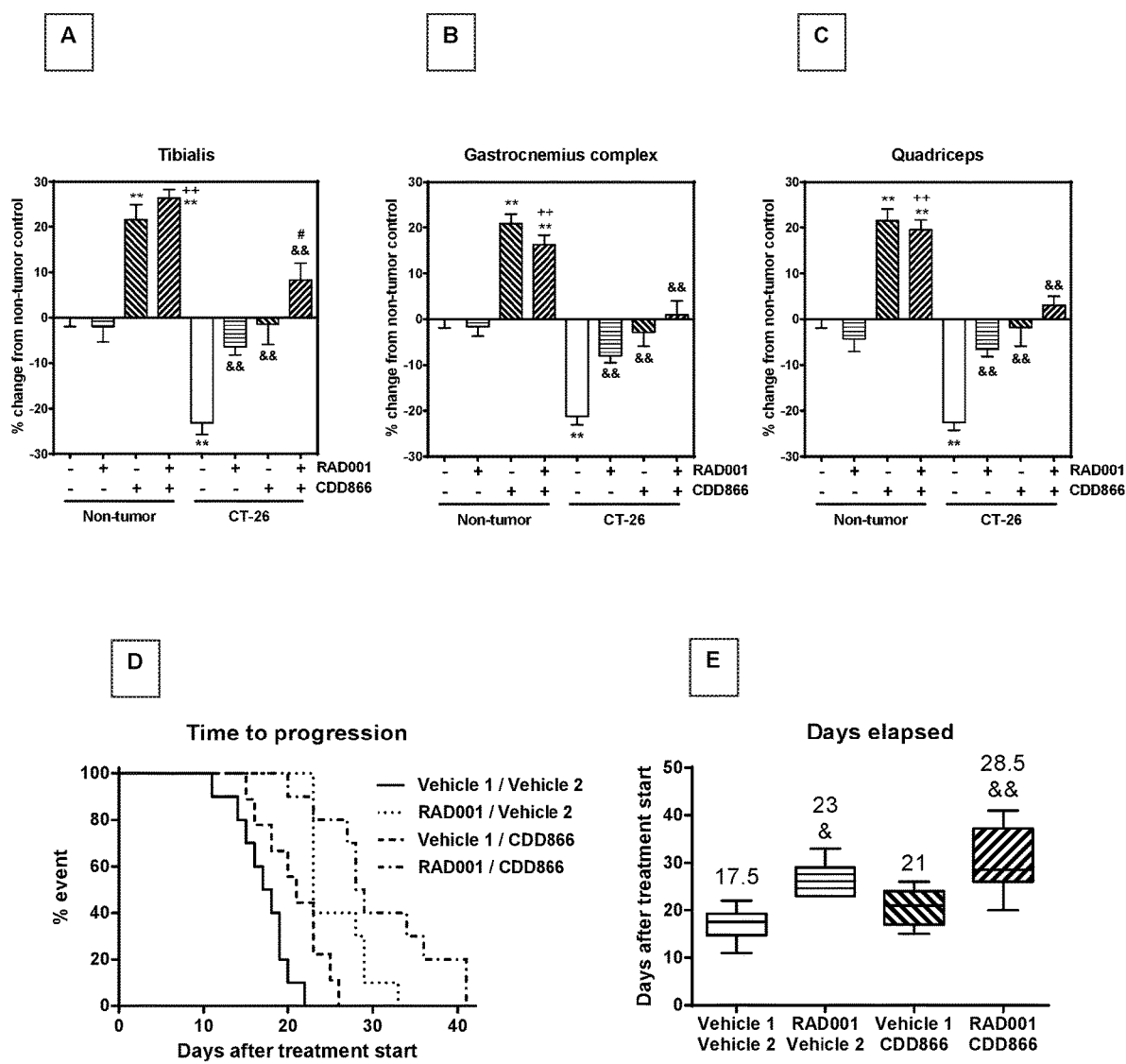
FIG. 4: The effects of everolimus and CDD866 on muscle weight and time-to-progression in CT-26 mouse colon cancer-induced cachexia, either alone or in combination. Values are expressed as means±SEM (n=10). Percent changes of muscle weight, normalized to initial body weight on day 0, were calculated in comparison to Non-tumor control (A, B, C); *: P<0.05, **: P<0.01 versus Non-tumor control; $^{\&}$: P<0.05, $^{\&\&}$: P<0.01 versus CT-26 control; $^{++}$: P<0.01 versus Non-tumor everolimus; $^{\times\times}$: P<0.01 versus Non-tumor CDD866; $^{\#\#}$: P<0.01 versus CT-26 everolimus; $^{\$}$: P<0.05, $^{\$\$}$: P<0.01 versus CT-26 CDD866 by Sidak's multiple comparison test following ANOVA. Time-to-progression expressed by % event defined by interruption criteria (D); median days elapsed before reaching an interruption criterion (E), expressed by box and whiskers with min to max (n=10); $^{\&}$: P<0.05, $^{\&\&}$: P<0.01 versus CT-26 control (Vehicle 1/Vehicle 2) by Dunn's multiple comparison test following ANOVA.

In the non-tumor bearing group, the weight of tibialis anterior, gastrocnemius-soleus-plantaris complex and quadriceps muscles was not affected by everolimus treatment and significantly increased by CDD866 treatment (FIG. 4A-C). The effect of CDD866 on muscle weight was maintained in the presence of everolimus. CT-26 tumor induced a significant decrease in the weight of tibialis anterior, gastrocnemius-soleus-plantaris complex and quadriceps muscles compared to the non-tumor bearing control group (FIG. 4A-C). CT-26-induced muscle weight loss was significantly reduced by everolimus or CDD866 treatment. Interestingly the combination of everolimus and CDD866 appeared to reverse skeletal muscle weight loss in an additive way, and the effect of the combined treatment was significantly different from the everolimus treatment alone.

Example 5

Bimagrumab in Combination with Everolimus Delays Time to Progression in Cancer Cachexia In addition to the beneficial effects of everolimus and CDD866 on CT-26-induced cachexia in the therapeutic intervention study, the effect of these treatments on progression of cancer and the associated cachexia was evaluated, using the same criteria as used in the cisplatin combination study. In the CT-26 control group, the median days elapsed until an interruption criterion (time-to-progression) was 17.5 days after randomization and treatment start (FIGS. 4D and E). Everolimus treatment significantly prolonged time-to-progression to 23 days mainly due to its anti-tumor effect, while CDD866 showed only a non-significant trend of extension to 21 days. The lack of significance of CDD866 on time-to-progression is explained by the fact that, although the treatment was highly successful in preventing body weight loss, it did not inhibit tumor growth, which was the $2^{nd}$ interruption criterion. Importantly, the combination of everolimus and CDD866 appeared to further slow time-to-progression to 28.5 days, an effect which was significant compared to the CT-26 control group.

Combination with Everolimus

Since mTOR is known to play a pivotal role in cell growth and proliferation, mTOR inhibition by everolimus exhibited significant anti-tumor effect as expected, both in the absence and presence of CDD866. This result clearly shows that anti-cancer effect of everolimus is not affected negatively by ActRII inhibition with CDD866. In line with body weight decreases caused by CT-26 tumor, skeletal muscle weight was significantly decreased in the CT-26 control group. Everolimus or CDD866 treatment alone significantly protected the tumor-bearing mice against skeletal muscle weight loss caused by CT-26 tumor. Interestingly, ActRII inhibition by CDD866 not only remains efficacious in the presence of everolimus but also showed a non-significant trend for an additive effect on reversing skeletal muscle weight loss, despite the fact that mTOR is required for normal muscle growth. Similarly, in the non-tumor-bearing mice, there was no effect on body weight by everolimus treatment, while CDD866 increased body weight significantly. The effect of CDD866 on body weight was maintained in the presence of everolimus, clearly showing that the mTOR inhibition did not alter the effect of CDD866 on body weight. Also the muscle anabolic response observed upon CDD866 treatment in non-tumor bearing mice was significant and not affected by mTOR inhibition at dose clearly effective on tumor.

Everolimus treatment alone prolonged time-to-progression as a surrogate for survival and also CDD866 showed a trend of extension. Importantly, the combination of everolimus and CDD866 appeared to further slow-down time-to-progression. Each treatment worked complementary to exert the beneficial effect, with everolimus inhibiting tumor growth and CDD866 preventing cachexia. A trend for an additive anti-cachectic effect observed in the combination of CDD866 and everolimus needs further exploration on how ActRII blockade and mTOR inhibition interacts positively on skeletal muscle undergoing cachexia.

It is reported that mTORC1 is activated denervation-induced skeletal muscle atrophy, but anti-atrophy effect of mTOR inhibition by rapamycin treatment was inconclusive. Activation of mTOR is also reported in other pathological conditions, such as aging, obesity, insulin resistance and diabetes, where mTOR inhibition seems to be beneficial. In the present study, there was a significant increase in phosphorylation as well as total amount of mTOR in the tumor-bearing mice. Therefore, it could be that such aberrant activation of mTOR in CT-26 colon cancer-induced cachexia also contributes to cachexia caused by cells, and therefore mTOR inhibition showed an additional benefit when combined with ActRII blockade.

Example 6

Combination of an mTOR Inhibitor and a Myostatin Antagonist in Ageing

The combination of bimagrumab and mTOR inhibitors such as everolimus may be particularly effective for the treatment of aging-related muscle dysfunction because bimagrumab increases muscle mass and everolimus improves muscle quality. Bimagrumab improves muscle mass by inhibiting the myostatin/activin pathway. Everolimus improves muscle function by inhibiting the mTOR pathway which is over-active in old muscle. Inhibition of mTOR may improve muscle function by enhancing mitochondrial function, decreasing inflammation and increasing autophagy. Improving muscle mass and function with the combination of bimagrumab and mTOR inhibitors such as everolimus is likely to have therapeutic benefit in sarcopenia and heart failure. In addition, improving muscle mass and function may have therapeutic benefit in diabetes mellitus by increasing glucose uptake in muscle.

Figure 5:
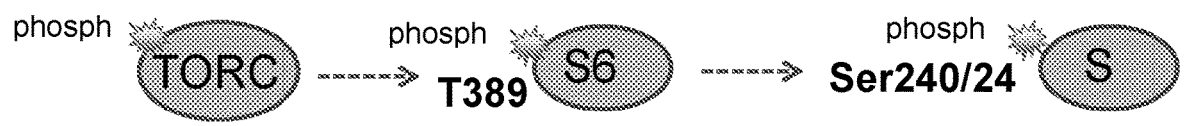
FIG. 5: mTOR is overexpressed in muscle of old vs young rats.
Figure 5:
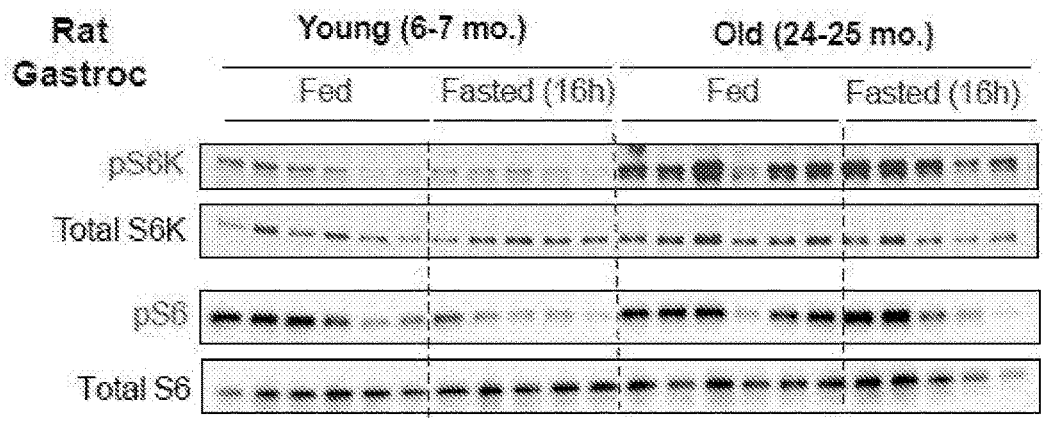

The data in FIG. 5 supports the rationale for the beneficial use of an mTOR inhibitors and a myostatin/activin pathway antagonist (e.g., bimagrumab) in aging, and shows that:
1. mTOR is overactive in skeletal muscle of old vs young rats
2. mTOR is not appropriately down regulated after fasting in the skeletal muscle of old vs young rats.

REFERENCES

The entire content of the following references, in particularly their definitions and descriptions in relation to, are incorporated herein by reference.
1. Fearon, K. et al. Definition and classification of cancer cachexia: an international consensus. *Lancet Uncool.* 12, 489-495 (2011).
2. Tan, B. H., Birdsell, L A., Martin, L., Baracos, V. E. & Fearon, K. C. Sarcopenia in an overweight or obese patient is an adverse prognostic factor in pancreatic cancer. *Clin. Cancer Res.* 15,: 6973-6979 (2009).
3. Benny Klimek, M. E. et al. Acute inhibition of myostatin-family proteins preserves skeletal muscle in mouse models of cancer cachexia. *Biochem. Biophys. Res. Commun.* 391, 1548-1554 (2010).
4. Busquets, S. et al. Myostatin blockage using actRIIB antagonism in mice bearing the Lewis lung carcinoma results in the improvement of muscle wasting and physical performance. J. Cachexia *Sarcopenia Muscle.* 3, 37-43 (2012).
5. Murphy, K. T. et al. Antibody-directed myostatin inhibition enhances muscle mass and function in tumor-bearing mice. *Am. J. Physiol. Regul. Integr. Comp.* 301, R716-R726 (2011).
6. Zhou, X. et al. Reversal of cancer cachexia and muscle wasting by ActRIIB antagonism leads to prolonged survival. *Cell.* 142, 531-543 (2010).
7. Elkina, Y., von Haehling, S., Anker, S. D. & Springer, J. The role of myostatin in muscle wasting: an overview. *J. Cachexia Sarcopenia Muscle.* 2, 143-151 (2011).
8. Lee, S. J. & McPherron, A. C. Regulation of myostatin activity and muscle growth. *Proc. Natl. Acad. Sci. U.S.A.* 98, 9306-9311 (2011).
9. Schuelke, M. et al. Myostatin mutation associated with gross muscle hypertrophy in a child. *N. Engl. J. Med.* 350, 2682-2688 (2004).
10. Whittemore, L. A. et al. Inhibition of myostatin in adult mice increases skeletal muscle mass and strength. *Biochem. Biophys. Res. Commun.* 300, 965-971 (2003).
11. Lee, S. J. et al. Regulation of muscle growth by multiple ligands signaling through activin type II receptors. *Proc. Natl. Acad. Sci. U.S.A.* 102, 18117-18122 (2005).
12. Nakatani, M. et al. Transgenic expression of a myostatin inhibitor derived from follistatin increases skeletal muscle mass and ameliorates dystrophic pathology in mdx mice. *FASEB J.* 22, 477-487 (2007).
13. Zimmers, T. A. et al. Induction of cachexia in mice by systemically administered myostatin. *Science.* 296, 1486-1488 (2002).
14. Chen, J. L. et al. Elevated expression of activins promotes muscle wasting and cachexia. *FASEB J.* 28, 1711-1723 (2014).
15. Lach-Trifilieff, E. et al. An antibody blocking activin type II receptors induces strong skeletal muscle hypertrophy and protects from atrophy. *Mol. Cell. Bio.* 34, 606-618 (2014).
16. Amato, A. A. et al. Treatment of sporadic inclusion body myositis with bimagrumab. *Neurology.* 83, 2239-2246 (2014).
17. Arrieta O. et al. Nutritional Status, Body Surface, and Low Lean Body Mass/Body Mass Index Are Related to Dose Reduction and Severe Gastrointestinal Toxicity Induced by Afatinib inPatients With Non-SmallCell LungCancer, *The Oncologist* 20, 967-974 (2015).
18. Sjoblom et al. Low muscle mass is associated with chemotherapy-induced haematological toxicity in advanced non-small cell lung cancer. *Lung Cancer* 90 85-91 (2015)
19. Parsons H A, Tsimberidou A M, Fu S, Hong D, Wen S, Baracos V E, Kurzrock R. Evaluation of the clinical relevance of body composition parameters in patients with cancer metastatic to the liver treated with hepatic arterial infusion chemotherapy. *Nutr Cancer;* 64: 206-17 (2012).
20. Reis, F. M. et al. Serum and tissue expression of activin a in postmenopausal women with breast cancer. *J. Clin. EndocrinoL Metab.* 87, 2277-2282 (2002).
21. Tsai, S. Importance of lean body mass in the oncologic patient. *Nutr. Clin. Pract.* 27, 593-598 (2012).
22. Bentzinger, C. F. et al. Skeletal muscle-specific ablation of raptor, but not of rictor, causes metabolic changes and results in muscle dystrophy. *Cell Metab.* 8, 411-424 (2008).
23. Risson, V. et al. Muscle inactivation of mTOR causes metabolic and dystrophin defects leading to severe myopathy. *J. Cell Biol.* 187, 859-874 (2009).
24. Argadine, H. M., Mantilla, C. B., Zhan, W. Z. & Sieck, G. C. Intracellular signaling pathways regulating net protein balance following diaphragm muscle denervation. *Am. J. Physiol. Cell Physiol.* 300, C318-327 (2011).
25. Machida, M. et al. Reduction of ribosome biogenesis with activation of the mTOR pathway in denervated atrophic muscle. *J. Cell Physiol.* 227, 1569-1576 (2012).
26. MacDonald, E. M. et al. Denervation atrophy is independent from Akt and mTOR activation and is not rescued by myostatin inhibition. *Dis. Model. Mech.* 7, 471-481 (2014).
27. Tang, H. et al. mTORC1 promotes denervation-induced muscle atrophy through a mechanism involving the activation of FoxO and E3 ubiquitin ligases. *Sci. Signal.* 7, ra18 (2014).
28. Nacarelli, T., Azar, A. & Sell, C. Aberrant mTOR activation in senescence and aging: A mitochondrial stress response? *Exp. Gerontol.* 68, 66-70 (2015).
29. Khamzina, L., Veilleux, A., Bergeron, S. & Marette, A. Increased activation of the mammalian target of rapamycin pathway in liver and skeletal muscle of obese rats: possible involvement in obesity-linked insulin resistance. *Endocrinology.* 146, 1473-1481 (2005).
30. Drake, J. C., Always, S. E., Hollander, J. M. & Williamson, D. L. AICAR treatment for 14 days normalizes obesity-induced dysregulation of TORC1 signaling and translational capacity in fasted skeletal muscle. *Am. J. Physiol. Regul. Integr. Comp. Physiol.* 299, R1546-1554 (2010).
31. Markofski M. et al. Effect of age on basal muscle protein synthesis and mTORC1 signaling in a large cohort of young and older men and women. Exp. Geront. 65, 1-7. 2015

SEQUENCE LISTING

```
<160> NUMBER OF SEQ ID NOS: 9

<210> SEQ ID NO 1
<211> LENGTH: 10
<212> TYPE: PRT
<213> ORGANISM: Artificial
<220> FEATURE:
<223> OTHER INFORMATION: Heavy chain CDR1
```

```
<400> SEQUENCE: 1

Gly Tyr Thr Phe Thr Ser Ser Tyr Ile Asn
1               5                   10

<210> SEQ ID NO 2
<211> LENGTH: 17
<212> TYPE: PRT
<213> ORGANISM: Artificial
<220> FEATURE:
<223> OTHER INFORMATION: Heavy chain CDR2

<400> SEQUENCE: 2

Thr Ile Asn Pro Val Ser Gly Ser Thr Ser Tyr Ala Gln Lys Phe Gln
1               5                   10                  15

Gly

<210> SEQ ID NO 3
<211> LENGTH: 6
<212> TYPE: PRT
<213> ORGANISM: Artificial
<220> FEATURE:
<223> OTHER INFORMATION: Heavy chain CDR3

<400> SEQUENCE: 3

Gly Gly Trp Phe Asp Tyr
1               5

<210> SEQ ID NO 4
<211> LENGTH: 14
<212> TYPE: PRT
<213> ORGANISM: Artificial
<220> FEATURE:
<223> OTHER INFORMATION: Light chain CDR1

<400> SEQUENCE: 4

Thr Gly Thr Ser Ser Asp Val Gly Ser Tyr Asn Tyr Val Asn
1               5                   10

<210> SEQ ID NO 5
<211> LENGTH: 11
<212> TYPE: PRT
<213> ORGANISM: Artificial
<220> FEATURE:
<223> OTHER INFORMATION: Light chain CDR2

<400> SEQUENCE: 5

Leu Met Ile Tyr Gly Val Ser Lys Arg Pro Ser
1               5                   10

<210> SEQ ID NO 6
<211> LENGTH: 10
<212> TYPE: PRT
<213> ORGANISM: Artificial
<220> FEATURE:
<223> OTHER INFORMATION: Light chain CDR3

<400> SEQUENCE: 6

Gly Thr Phe Ala Gly Gly Ser Tyr Tyr Gly
1               5                   10

<210> SEQ ID NO 7
<211> LENGTH: 217
<212> TYPE: PRT
<213> ORGANISM: Artificial
<220> FEATURE:
```

<223> OTHER INFORMATION: light chain

<400> SEQUENCE: 7

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 8
<211> LENGTH: 217
<212> TYPE: PRT
<213> ORGANISM: Artificial
<220> FEATURE:
<223> OTHER INFORMATION: light chain

<400> SEQUENCE: 8

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125
```

Glu Leu Gln Ala Asn Lys Ala Thr Leu Val Cys Leu Ile Ser Asp Phe
            130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
            195                 200                 205

Lys Thr Val Ala Pro Thr Glu Cys Ser
210                 215

<210> SEQ ID NO 9
<211> LENGTH: 445
<212> TYPE: PRT
<213> ORGANISM: Artificial
<220> FEATURE:
<223> OTHER INFORMATION: heavy chain

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Thr Ile Asn Pro Val Ser Gly Ser Thr Ser Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Gly Gly Trp Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Arg Val Glu Pro Lys Ser Cys Asp Lys Thr His Thr Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

```
Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305             310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445
```

The invention claimed is:

1. A pharmaceutical combination comprising a) an ActRII receptor inhibitor and b) a chemotherapeutic agent, wherein the ActRII receptor inhibitor and the chemotherapeutic agent are in separate form, wherein the ActRII receptor inhibitor is an anti-ActRII receptor antibody, and wherein the chemotherapeutic agent is an mTOR inhibitor.

2. The combination according to claim 1, wherein the anti-ActRII receptor antibody is bimagrumab.

3. The combination according to claim 1, wherein the mTOR inhibitor is everolimus.

4. A method of treating a subject having an age-related muscle dysfunction, comprising administering to the subject an anti-ActRII receptor antibody and an mTOR inhibitor.

5. The method of claim 4, wherein the anti-ActRII receptor antibody is bimagrumab.

6. The method of claim 4, wherein the mTOR inhibitor is everolimus.

7. The combination of claim 1, wherein the anti-ActRII receptor antibody comprises the amino acid sequences of SEQ ID NOs: 1-3 and 4-6.

8. The combination of claim 1, wherein the anti-ActRII receptor antibody comprises the amino acid sequences of SEQ ID NOs: 7 or 8 and SEQ ID NO: 9.

9. The method of claim 4, wherein the anti-ActRII receptor antibody comprises the amino acid sequences of SEQ ID NOS: 1-3 and 4-6.

10. The method of claim 4, wherein the anti-ActRII receptor antibody comprises the amino acid sequences of SEQ ID NOs: 7 or 8 and SEQ ID NO: 9.

11. The method of claim 4, wherein the anti-ActRII antibody and the mTOR inhibitor are in separate form.

* * * * *